(12) United States Patent
Fiscus et al.

(10) Patent No.: US 9,068,033 B2
(45) Date of Patent: Jun. 30, 2015

(54) BRANCHED POLYETHYLENE WITH IMPROVED PROCESSING AND HIGH TEAR FILMS MADE THEREFROM

(71) Applicant: ExxonMobil Chemical Patents Inc., Baytown, TX (US)

(72) Inventors: David M. Fiscus, Houston, TX (US); Laughlin G. McCullough, League City, TX (US); John F. Walzer, Jr., Seabrook, TX (US); Jay L. Reimers, Houston, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/091,105

(22) Filed: Nov. 26, 2013

(65) Prior Publication Data

US 2014/0179872 A1    Jun. 26, 2014

Related U.S. Application Data

(60) Provisional application No. 61/740,916, filed on Dec. 21, 2012.

(51) Int. Cl.
*C08F 210/16*    (2006.01)
*C08L 23/16*    (2006.01)
(Continued)

(52) U.S. Cl.
CPC .............. *C08F 210/16* (2013.01); *C08F 4/76* (2013.01); *C08L 23/0815* (2013.01); *C08F 4/65912* (2013.01); *C08F 4/65916* (2013.01)

(58) Field of Classification Search
CPC ........ C08F 210/16; C08F 4/76; C08F 210/02; C08F 210/04; C08F 210/14; C08L 23/0815; C08L 2205/00

USPC .......................................................... 526/348
See application file for complete search history.

(56) References Cited

U.S. PATENT DOCUMENTS

| 5,272,236 A | 12/1993 | Lai et al. |
| 5,444,145 A | 8/1995 | Brant et al. |

(Continued)

FOREIGN PATENT DOCUMENTS

| JP | 2011089019 A | 5/2011 |
| JP | 2011137146 | 7/2011 |

(Continued)

OTHER PUBLICATIONS

Bersted, B.H. et al., "Prediction of Rheological Behavior of Branched Polyethylene from Molecular Structure", Journal of Applied Polymer Science, vol. 26, 1981, pp. 1001-1014.
(Continued)

*Primary Examiner* — Nathan M Nutter
(74) *Attorney, Agent, or Firm* — Kevin M. Faulkner; Catherine L. Bell

(57) ABSTRACT

This invention relates to inventive ethylene-based copolymers comprising 75.0 wt % to 99.5 wt % of ethylene-derived units and 0.5 wt % to 25.0 wt % of C3 to C20 olefin derived units; the inventive ethylene-based copolymer having: a density in the range of from 0.900 to less than 0.940 g/cm$^3$; a g'(vis) of less than 0.80; a melt index, $I_2$, of from 0.25 to 1.5 g/10 min.; a Mw/Mn within a range from 3.0 to 6.0, and Mz/Mn greater than 8.0; and an absence of a local minimum loss angle at a complex modulus, G*, of $1.00 \times 10^4$ to $3.00 \times 10^4$ Pa.

17 Claims, 15 Drawing Sheets

(51) Int. Cl.
  *C08F 4/76* (2006.01)
  *C08L 23/08* (2006.01)
  *C08F 4/659* (2006.01)

(56) References Cited

U.S. PATENT DOCUMENTS

| | | | |
|---|---|---|---|
| 5,475,075 | A | 12/1995 | Brant et al. |
| 6,114,477 | A | 9/2000 | Merrill et al. |
| 6,908,972 | B2 | 6/2005 | Tsuie et al. |
| 2008/0249262 | A1 | 10/2008 | Chai |
| 2010/0292421 | A1 | 11/2010 | Bando |
| 2011/0009580 | A1 | 1/2011 | Chai |
| 2013/0041119 | A1 | 2/2013 | Ochi et al. |
| 2013/0072632 | A1* | 3/2013 | Wang et al. ............ 525/53 |
| 2013/0085244 | A1 | 4/2013 | Zhao et al. |
| 2013/0090433 | A1 | 4/2013 | Jiang et al. |
| 2013/0211009 | A1 | 8/2013 | Yang et al. |
| 2013/0224463 | A1* | 8/2013 | Shirodkar et al. ............ 428/220 |

FOREIGN PATENT DOCUMENTS

| | | |
|---|---|---|
| JP | 2011-225670 | 11/2011 |
| WO | WO 99-35174 | 7/1999 |
| WO | 2012/133717 | 10/2012 |

OTHER PUBLICATIONS

Donati, G. et al., "Scale up of chemical reactors", Catalysis Today, 1997, Chapter 17, pp. 483-533.

Gabriel, C. et al., "Analytical and rheological characterization of long-chain branched metallocene-catalyzed ethylene homopolymers", Polymer, 43, 2002, pp. 6383-6390.

Kaylon, D. et al., "High Pressure Polymerization of Ethylene and Rheological Behavior of Polyethylene Product", Polymer Engineering and Science, May 1994, vol. 34, No. 10, pp. 804-814.

Kokko, E. et al., "Structural Analysis of Polyethene Prepared with *rac*Dimethylsilylbis(indenyl)zirconium Dichloride/Methylaluminoxane in a High-Temperature, Continuously Stirred Tank Reactor", Journal of Polymer Science: Part A: Polymer Chemistry, vol. 40, 2002, pp. 3292-3301.

Kolhapure, N. et al., "PDF Simulations of Ethylene Decomposition in Tubular LDPE Reactors", AIChE Journal, Feb. 2005, vol. 51, No. 2, pp. 585-606.

Lee, H. et al., "Modeling of Industrial High Pressure Autoclave Polyethylene Reactor Including Decomposition Phenomena", Korean J. Chem. Eng., 17(2), 2000, pp. 223-229.

Lenz, R., "Applied Reaction Kinetics Polymerization Reaction Kinetics", Ind. Eng. Chem., Mar. 1969, vol. 61, No. 3, pp. 67-75.

Maschio, G. et al., "Analysis of the molecular weight distribution in free radical polymerization: Modelling of the MWD from the analysis of experimental GPC curves", Macromol. Chem. Phys. 200, 1999, No. 7, pp. 1708-1721.

Kim, D. et al., "Modeling of branching density and branching distribution in low-density polyethylene polymerization", Chemical Engineering Science, 63, 2008, pp. 2035-2046.

Ogo, Y., "Polymerizations at High Pressures", JMS-Rev. Macromol. Chem. Phys., C24(1), 1984, pp. 1-48.

Tiang, J. et al., "Evaluating the Processability of Film Blowing Resins", Polymer Engineering and Science, 2009, 49, pp. 2132-2143.

Wang, W. et al., "Kinetics of Long Chain Branching in Continuous Solution Polymerization of Ethylene Using Constrained Geometry Metallocene", Macromolecules, 1998, 31, pp. 8677-8683.

White, J. et al., "Orientation, Crystallization, and Haze Development in Tubular Film Extrusion", Advances in Polymer Technology, vol. 8, No. 1, 1988, pp. 27-61.

Yan, D. et al., "Effect of long chain branching on rheological properties of metallocene polyethylene", Polymer, 40, 1999, pp. 1737-1744.

Zavala, V. et al., "Optimization-based strategies for the operation of low-density polyethylene tubular reactors: Moving horizon estimation", Computers and Chemical Engineering, 33, 2009, pp. 379-390.

Zavala, V. et al., "Large-Scale Parameter Estimation in Low-Density Polyethylene Tubular Reactors", Ind. Eng. Chem. Res., 2006, 45, pp. 7867-7881.

Zhou, W. et al., "Modeling LDPE Tubular and Autoclave Reactors", Ind. Eng. Chem. Res., 2001, 40, pp. 5533-5542.

Gujarathi, Ashish M. et al., "*Modeling and Simulation of Low Density Polyethylene (LDPE) High Pressure Tubular Reactor*," CHEMCON, 2008.

Meimaroglou, Dimitrios et al., "Prediction of Bivariate Molecular Property Distributions in Free-Radical Polymerization Systems Using Monte Carlo and Sectional Grid Methods," Chemical Product and Process Modeling, vol. 3, 2008, Iss. 1, Art. 44, pp. 1-29.

Piel, Christian, "*Polymerization of Ethene and Ethene-co-α-Olefin: Investigations on Short-and Long-Chain Branching and Structure-Property Relationships*," Dissertation, Hamburg 2005.

Yang, Q. et al., "*Alternative View of Long Chain Branch Formation by Metallocene Catalysts*," Macromolecules, 2010, vol. 43, pp. 8836-8852.

\* cited by examiner

BRANCHED POLYETHYLENE WITH IMPROVED PROCESSING AND HIGH TEAR FILMS MADE THEREFROM

CROSS-REFERENCE TO RELATED APPLICATIONS

This application claims the benefit of Provisional Application No. 61/740,916, filed Dec. 21, 2012 and EP 13160928.1 filed Mar. 25, 2013.

This application relates to U.S. Ser. No. 61/740,938, filed on Dec. 21, 2012.

FIELD OF THE INVENTION

This invention relates to branched polyethylenes produced at low pressure and temperature using a metallocene compound and films produced therefrom, in particular blown film.

BACKGROUND OF THE INVENTION

Various types of polyethylenes are known in the art and each type has various applications. For example, low density polyethylene is generally prepared at high pressure using free radical initiators (known in the industry as "LDPE"). LDPE is also known as "branched" or "heterogeneously branched" polyethylene because of the relatively large number of branches extending from the polymer backbone. Polyethylene in the same density range, i.e., 0.916 to 0.950 g/cm$^3$, which is linear and does not contain long chain branching is known as "linear low density polyethylene" ("LLDPE") and may be produced, for example in a gas phase process, with conventional Ziegler-Natta catalysts or with metallocene compounds.

A large portion of global LDPE demand includes film, carrying bag, and sack applications. Some examples of these applications include agricultural, multi-layer, and shrink films, as well as reinforcements for levees. LDPE, which is soft, ductile, and flexible, is additionally utilized for strong, elastic goods, such as screw caps, lids, and coatings. Films made from LDPE, however, have limited impact resistance compared to the catalyst produced LLDPEs. Likewise, LLDPE's have a high impact resistance but are difficult to process. Blending these resins often creates a composition that is easier to process, but the desirable toughness of the LLDPE's is reduced. What would be desirable is to improve the processability of LLDPE-type resins while maintaining high tear and toughness in the films produced from such resins.

Thus, there is a need for new efficient and cost advantageous processes to produce polymers having a density from 0.900 to 0.950 g/cm$^3$ that are strong but have improved processing. More specifically, there is a need for new and improved products produced from these branched polymers, in particular blown film.

Related references include U.S. Pat. No. 6,908,972, US 2013-0090433, US 2013-0085244, US 2013-0211009, US 2013-041119, WO 2012-133717, JP 2011225670A, JP2011089019A, JP2011137146, and Q. Yang et al. in 43 MACROMOLECULES 8836-8852 (2010).

SUMMARY OF THE INVENTION

This invention relates to ethylene-based copolymers made in a low pressure catalytic process that are low to medium density, have a large degree of branching, some bimodal-aspects such that it has a high molecular weight portion associated with the polymer, and shear thinning characteristics. These characteristics result in a polyethylene polymer that is strong (high Modulus, Dart Drop) and easily processible (lower melt temperature, motor load for given production rate). These features are quantified by having a density in the range of from 0.900 to less than 0.940 g/cm$^3$; a g'(vis) of less than 0.80; a Mz/Mn of greater than 8.0; and an absence of a local minimum loss angle at a complex modulus, G*, of $1.00 \times 10^4$ to $3.00 \times 10^4$ Pa. The ethylene-based copolymer comprises within the range from 75.0 wt % to 99.5 wt % of ethylene-derived units and 0.5 wt % to 25.0 wt % of $C_3$ to $C_{20}$ olefin derived units.

This invention also relates to polymer blend compositions comprising from 0.5 wt % to 99.9 wt % of an inventive ethylene-based copolymer and from 0.1 wt % to 99.5 wt % of a polymer preferably selected from the group consisting of high density polyethylene, linear low density polyethylene, low density polyethylene, medium density polyethylene, and combinations thereof.

This invention yet further relates to a film comprising at least 5 wt % of an inventive ethylene-based copolymer wherein the film has a 1% Secant Modulus MD of 30,000 psi or greater; an Elmendorf Tear MD value of 100 g/mil or greater; and a Dart Impact of 225 g/mil or greater. Desirably, the films exhibit the relationship of having a Dart Drop (g/mil) of greater than −8.09×[Average Elmendorf Tear (g/mil)]+853.81.

DETAILED DESCRIPTION

Figure 1:
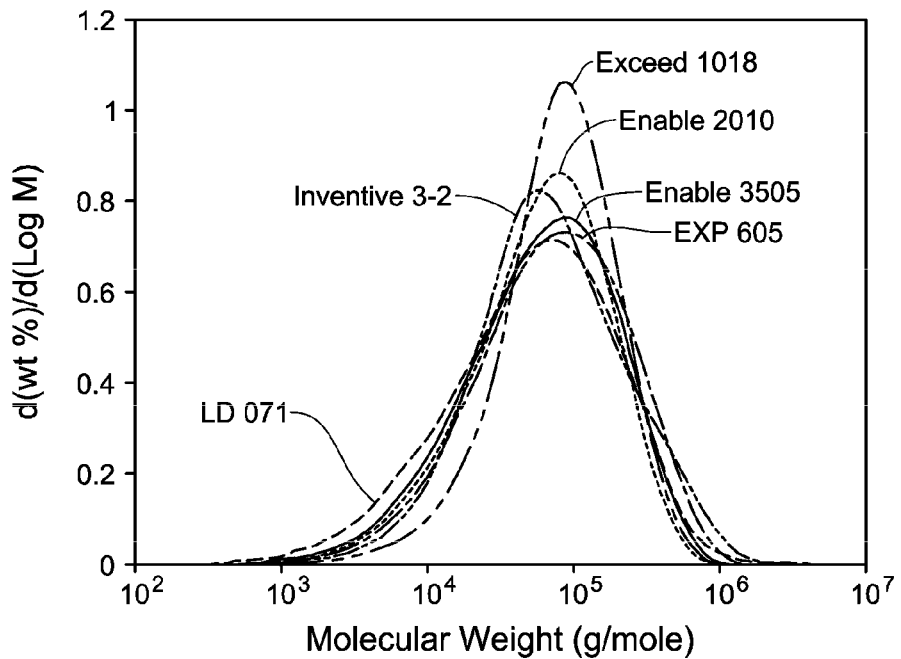
FIG. 1 shows the GPC chromatogram of the inventive resin 3-2 compared with comparative commercial resins.

LDPE is typically produced in a tubular reactor system using a free radical initiator under conditions of very high pressure and temperature. The inventors have surprisingly found a branched low density polyethylene (the invention resin referred to as an "ethylene-based copolymer", or "LCB m-LLDPE") can be produced under less extreme conditions by, for example, a metallocene-driven catalytic process. In particular, this ethylene-based copolymer may be produced in gas phase polymerization processes. The ability to produce ethylene-based copolymer using gas phase polymerization systems is particularly advantageous because the production rate can be much greater than that achievable in tubular reactors, at lower pressures and temperatures. This increased productivity coupled with being able to run at reduced temperatures and pressures provides a significant cost advantage for ethylene-based copolymers in the gas phase over traditional LDPEs.

The inventors further discovered that these ethylene-based copolymer resins and blends thereof proved to have several processing advantages including reduced motor load, die pressure, torque, and head pressure. These advantages all lead to less wear on the processing equipment which reduces replacement cost and down time. Even more advantageously, films made from these ethylene-based copolymer resins demonstrate excellent physical properties such as tear performance, dart impact, stiffness, and haze. Each of the polymer, process to produce the polymer, blends of the polymer (both physical and in-reactor), and films made from the polymer are discussed below.

Polymerization Process

The inventive ethylene-based copolymer are preferably made in a process comprising contacting ethylene and of one or more $C_3$ to $C_{20}$ olefins in at least one gas phase reactor at a temperature in the range of from 60° C. to 90° C. and at a reactor pressure of from 70 kPa to 7000 kPa, in the presence of a metallocene catalyst system comprising a bridged metallocene compound represented by the following formula:

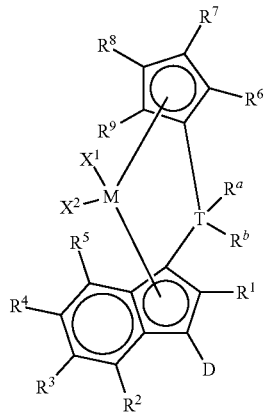

wherein:

M is a group 4 metal, especially zirconium or hafnium;

T is a group 14 atom;

D is hydrogen, methyl, or a substituted or unsubstituted aryl group, most preferably phenyl;

$R^a$ and $R^b$ are independently, hydrogen, halogen, or a $C_1$ to $C_{20}$ substituted or unsubstituted hydrocarbyl, and $R^a$ and $R^b$ can form a cyclic structure including substituted or unsubstituted aromatic, partially saturated, or saturated cyclic or fused ring system;

each $X^1$ and $X^2$ is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers, and $X^1$ and $X^2$ can form a cyclic structure including aromatic, partially saturated, or saturated cyclic or fused ring system;

each of $R^1$, $R^2$, $R^3$, $R^4$, and $R^5$ is, independently, hydrogen, halide, alkoxide or a $C_1$ to $C_{20}$ or $C_{40}$ substituted or unsubstituted hydrocarbyl group, and any of adjacent $R^2$, $R^3$, $R^4$, and/or $R^5$ groups may form a fused ring or multicenter fused ring systems, where the rings may be substituted or unsubstituted, and may be aromatic, partially unsaturated, or unsaturated; and each of $R^6$, $R^7$, $R^8$, and $R^9$ is, each independently, hydrogen or a $C_1$ to $C_{20}$ or $C_{40}$ substituted or unsubstituted hydrocarbyl group, most preferably methyl, ethyl or propyl; and further provided that at least two of $R^6$, $R^7$, $R^8$, and $R^9$ are $C_1$ to $C_{40}$ substituted or unsubstituted hydrocarbyl groups; wherein "hydrocarbyl" (or "unsubstituted hydrocarbyl") refers to carbon-hydrogen radicals such as methyl, phenyl, iso-propyl, napthyl, etc. (aliphatic, cyclic, and aromatic compounds consisting of carbon and hydrogen), and "substituted hydrocarbyl" refers to hydrocarbyls that have at least one heteroatom bound thereto such as carboxyl, methoxy, phenoxy, $BrCH_3$—, $NH_2CH_3$—, etc.

The polymerization process of the present invention may be carried out using any suitable process, such as, for example, solution, slurry, high pressure, and gas phase. A particularly desirable method for producing polyolefin polymers according to the present invention is a gas phase polymerization process preferably utilizing a fluidized bed reactor. Desirably, gas phase polymerization processes are such that the polymerization medium is either mechanically agitated or fluidized by the continuous flow of the gaseous monomer and diluent. Other gas phase processes contemplated by the process of the invention include series or multistage polymerization processes.

The metallocene catalyst is used with an activator in the polymerization process to produce the inventive polyethylenes. The term "activator" is used herein to be any compound which can activate any one of the metallocene compounds described above by converting the neutral catalyst compound to a catalytically active metallocene compound cation. Preferably the catalyst system comprises an activator. Activators useful herein include alumoxanes or so called "non-coordinating anion" activators such as boron-based compounds (e.g., tris(perfluorophenyl)borane, or ammonium tetrakis (pentafluorophenyl)borate).

Preferred activators typically include alumoxane compounds (or "alumoxanes") and modified alumoxane compounds. Alumoxanes are generally oligomeric compounds containing —$Al(R^1)$—O— sub-units, where $R^1$ is an alkyl group. Examples of alumoxanes include methylalumoxane (MAO), modified methylalumoxane (MMAO), ethylalumoxane, isobutylalumoxane, and mixtures thereof. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. Another useful alumoxane is a modified methylalumoxane (MMAO) cocatalyst type 3A (commercially available from Akzo Chemicals, Inc. under the trade name Modified Methylalumoxane type 3A, disclosed in U.S. Pat. No. 5,041,584). Preferably of this invention, the activator is an alkylalumoxane, preferably methylalumoxane or isobutylalumoxane, most preferably methylalumoxane.

Preferably, the alumoxane activator is supported on a support material prior to contact with the metallocene compound. Also, the alumoxane activator is combined with the metallocene compound prior to being placed upon a support material. Preferably, the alumoxane activator may be combined with the metallocene compound in the absence of a support material.

In addition to these alumoxane activator compounds, cocatalysts may be used. Aluminum alkyl or organometallic compounds which may be utilized as cocatalysts (or scavengers) include, for example, triethylaluminum, tri-isobutylaluminum, tri-n-hexylaluminum, tri-n-octylaluminum, diethyl aluminum chloride, dibutyl zinc, diethyl zinc, and the like.

Preferably, the catalyst system comprises an inert support material. Preferably, the supported material is a porous support material, for example, talc, and inorganic oxides. Other support materials include zeolites, clays, organoclays, or any other organic or inorganic support material, or mixtures thereof.

Preferably, the support material is an inorganic oxide in a finely divided form. Suitable inorganic oxide materials for use in metallocene compounds herein include Groups 2, 4, 13, and 14 metal oxides such as silica, alumina, and mixtures thereof. Other inorganic oxides that may be employed, either alone or in combination, with the silica or alumina are magnesia, titania, zirconia, and the like. Other suitable support materials, however, can be employed, for example, finely divided functionalized polyolefins such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

The supported catalyst system may be suspended in a paraffinic agent, such as mineral oil, for easy addition to a reactor system, for example a gas phase polymerization system.

Processes and catalyst compounds useful in making the inventive polyethylenes are further described in U.S. Ser. No. 61/740,938, entitled "Bridged Metallocene Compounds, Catalyst Systems and Processes for Polymerization Therewith" filed on Dec. 21, 2012.

Inventive Ethylene-Based Copolymer

The present invention relates to ethylene-based polymers made in a low pressure catalytic process ("ethylene-based copolymer") comprising for example from 75.0 wt % to 99.5 wt % of ethylene-derived units and from 0.5 wt % to 25.0 wt % of $C_3$ to $C_{20}$ olefin derived units. The inventive ethylene-based copolymer typically have for example a density in the range of from 0.900 or 0.920 g/cm$^3$ to less than 0.950 g/cm$^3$; a g'(vis) of less than 0.80; a melt index, $I_2$, of from 0.25 to 1.5 g/10 min.; a Mw/Mn within a range from 3.0 to 6.0; an Mz/Mn of greater than 8, and preferably has an absence of a local minimum loss angle at a complex modulus, G*, of $1.00 \times 10^4$ to $3.00 \times 10^4$ Pa, where the ranges for each parameter for which may be within the various ranges as described herein. For Example, in FIG. 3B showing the Enable products contain gel-like material as indicated by the Enable products having " . . . a local minimum loss angle at a complex modulus, G*, of $1.00 \times 10^4$ to $3.00 \times 10^4$ Pa; whereas the inventive ethylene-based polymers do not contain the gel-like material as shown by the OMC-1480 resins having " . . . an absence of a local minimum loss angle at a complex modulus, G*, of $1.00 \times 10^4$ to $3.00 \times 10^4$ Pa . . . ". The " . . . absence of a local minimum loss angle at a complex modulus, G*, of $1.00 \times 10^4$ to $3.00 \times 10^4$ Pa . . . " indicates a strong interaction term according to Flory-Huggins Theory, that is, the long chain branched material is soluble in m-LLDPE material, while the appearance " . . . of a local minimum loss angle at a complex modulus, G*, of $1.00 \times 10^4$ to $3.00 \times 10^4$ Pa . . . " indicates a weak interaction term, i.e., the long chain branched material is not as soluble in m-LLDPE material. The Enable products have a local minimum loss angle indicating the branched material in those resins are not soluble in the m-LLDPE material, in other words, it is like a gel.

In any case, the inventive ethylene-based copolymer compositions herein preferably refer to a polyethylene copolymer having from 99.5 wt % to 75.0 wt % ethylene-derived units, more preferably from 99.0 wt % to 80.0 wt %, or 99.0 wt % to 85 wt %, or 99.0 wt % to 90.0 wt %, or 99.0 wt % to 92.5 wt %, or 99.0 wt % to 95.0 wt %, or 99.0 wt % to 97.0 wt % ethylene-derived units; and from 0.5 wt % to 25.0 wt % olefin derived units ($C_3$ to $C_8$ or $C_{20}$ olefins, preferably α-olefin), more preferably 1.0 wt % to 20.0 wt %, or 1.0 wt % to 15 wt %, or 1.0 wt % to 10.0 wt %, or 1.0 wt % to 7.5 wt %, or 1.0 wt % to 5.0 wt %, or 1.0 wt % to 3.0 wt % of $C_3$ to $C_{20}$ olefin derived units. The olefin may be linear or branched, and two or more comonomers may be used, if desired. Examples of suitable olefins include propylene, 1-butene, 1-pentene; 1-pentene with one or more methyl, ethyl, or propyl substituents; 1-hexene. Particularly suitable olefins include 1-butene, 1-hexene, and 1-octene, 1-hexene being most preferred. Examples of the inventive ethylene-based copolymers useful herein include: ethylene/butene, ethylene/hexene, ethylene/octene, ethylene/propylene/butene, ethylene/propylene/hexene, ethylene/butene/hexene, and ethylene/hexene/octane copolymers and terpolymers.

The inventive ethylene-based copolymers have a density within the range from 0.900 g/cm³ to 0.950 g/cm³, more preferably within a range from 0.910 or 0.915 or 0.920 or 0.925 or 0.930 or 0.935 g/cm³ to 0.940 or 0.945 or 0.950 g/cm³, determined using chips cut from plaques compression molded in accordance with ASTM D-1928 Procedure C, aged in accordance with ASTM D-618 Procedure A, and measured as specified by ASTM D-1505.

The ethylene-based copolymers are highly branched. The degree of long-chain branching in the inventive ethylene-based copolymers may be quantified by determination of the branching index, g', which is inversely proportional to the amount of branching. Thus, lower values for g' indicate relatively higher amounts of branching. The inventive ethylene-based copolymers have a g'(vis) of less than 0.80 (preferably less than 0.75, less than 0.70, less than 0.65, less than 0.60; and alternatively greater than 0.25, greater than 0.30, or greater than 0.35). The inventive ethylene-based copolymers may also have a g'(z avg) of less than 0.75 (preferably less than 0.70, less than 0.65, less than 0.60, less than 0.55; and alternatively greater than 0.10, greater than 0.15, or greater than 0.20). The two branching indices g'(vis) and g'(z avg) are defined as ratios of average intrinsic viscosities:

$$g' = \frac{\eta_b}{\eta_l}$$

where $\eta_b$ is the average intrinsic viscosity of the branched polymer and $\eta_l$ is the intrinsic viscosity of a linear polymer of the same viscosity-averaged molecular weight ($M_v$) as the branched polymer. In the averages, the intrinsic viscosity of a linear polypropylene is $KM_i^\alpha$, where K=0.0002288 and α=0.705. The viscosity averaged g' was calculated using the following equation:

$$g'_{vis} = \frac{\sum C_i[\eta_i]_b}{\sum C_i K M_i^\alpha}$$

where $C_i$ is the polymer concentration in the slice i in the polymer peak, and $[\eta_i]_b$ is the viscosity of the in-reactor blend in slice i of the polymer peak, and $M_i$ is the weight averaged molecular weight in slice i of the polymer peak measured by light scattering, α=0.695 and k=0.000579 for linear ethylene polymers, α=0.705 k=0.000262 for linear propylene polymers, and α=0.695 and k=0.000181 for linear butene polymers. See 34 MACROMOLECULES 6812-6820 (2001) and 38 MACROMOLECULES 7181-7183 (2005), for guidance on selecting a linear standard having similar molecular weight and comonomer content, and determining k coefficients and α exponents. The Z average g' was calculated using $C_i$=polymer concentration in the slice i in the polymer peak times the mass of the slice squared, $M_i^2$. G'(z avg) gives heavier weighting to the high molecular weight components of the blends. The g' values are below one when the polymer samples (polymer and diluent, heated and measured) are less viscous than samples of linear polyethylene, extrapolated as evidence of long-chain branching. Typically, g'(z avg) is smaller than g'(vis) because higher molecular weight chains are more likely to have long chain branches.

The inventive ethylene-based copolymers preferably have a melt index, $I_2$, of 0.25 to 1.5 g/10 min, more preferably 0.25 to 1.25 g/10 min or 0.10 to 1.10 g/10 min or more preferably 0.15 to 1.10 g/10 min, as determined in accordance with ASTM D-1238 under a load of 2.16 kg and at a temperature of 190° C. The inventive ethylene-based copolymers also have a high-load melt index, $I_{21}$, of 5.0 to 30.0 g/10 min, more preferably 7.0 to 25.0 g/10 min, or more preferably 9.0 to 20.0 g/10 min, as determined in accordance with ASTM D-1238 under a load of 21.6 kg and at a temperature of 190° C. The melt index ratio ($I_{21}/I_2$) of the inventive ethylene-based copolymers has a lower limit of 10.0 and an upper limit of 100.0. The lower limit on the melt index ratio may be 20.0, 25.0, 30.0, or 35.0. The upper limit on the melt index ratio may be 95.0, 90.0, 85.0, 80.0, 75.0, 70.0, 65.0, 60.0, 50.0, or 40.0. Any combination of lower and upper limits should be considered to be disclosed by the above limits on the melt index ratio, e.g. 35.0 to 90.0, 40.0 to 60.0, or 45.0 to 80.0, etc.

The inventive ethylene-based copolymers have a "molecular weight distribution" (or MWD) which means the ratio of Mw to number average molecular weight (Mn) or Mw/Mn. Mw and Mn are determined by GPC. Typically the inventive ethylene-based copolymers have a molecular weight distribution (MWD, defined as $M_w/M_n$) within a range from 3.0 to 6.0, or preferably within a range of from 3.0 or 3.2 or 3.4 to 4.2 or 4.6 or 5.0 or 5.5 or 6.0. The inventive ethylene-based copolymers preferably have a Mw of greater than 75,000 g/mol or 80,000 g/mol, or 85,000 g/mol or 90,000 g/mol. The inventive ethylene-based copolymers have a Mw of less than 1,000,000 g/mol or 500,000 g/mol, or 350,000 g/mol or 300,000 g/mol. As stated above, the ethylene-based copolymers preferably have a Mz/Mn of greater than 8.0 or 9.0 or 10.0, or within a range of from 5.0 or 6.0 or 7.0 to 8.0 or 9.0 or 10.0 or 11.0 or 12.0 or 14.0 or 16.0 or 18.0.

While the ethylene-based copolymers may be characterized by a value of the complex modulus at a particular loss angle as described below, another way to describe some inventive ethylene-based copolymers of the invention relates to features of the complex modulus values, G*, when considered over the range of loss angles from 30° to 90°. The inventive ethylene-based copolymers herein have an absence of a local minimum loss angle at a complex modulus, G*, of $1.00 \times 10^4$ to $3.00 \times 10^4$ Pa (see FIG. 3C). The inventive ethylene-based copolymers of this invention also have a complex modulus, $G^*_{50}$, greater than $50.00 \times 10^3$ Pa (preferably greater than $60.00 \times 10^3$ Pa, greater than $70.00 \times 10^3$ Pa, or greater than $75.00 \times 10^3$ Pa). Complex modulus, G*, and loss angles, δ, may be obtained from rheological data determined at the test temperature of 190° C. and analyzed using the Van Gurp-Palmen treatment (reference: M. Van Gurp and J. Palmen, 67 RHEOLOGY BULLETIN 5 (1998)), whereby the loss angle, δ, (wherein δ=arctan⁻¹(G"/G'); G" represents the loss modulus (Pa) and G' represents the storage modulus (Pa)) is plotted against the absolute value of the complex modulus $|G^*|=(G'^2+G''^2)^{1/2}$. This representation of linear viscoelastic data is a powerful means of characterizing molecular and structural features of polymers. For example, low levels of long-chain branching in polyolefins can be detected and quantified on a relative basis, using this methodology.

Figure 2A:
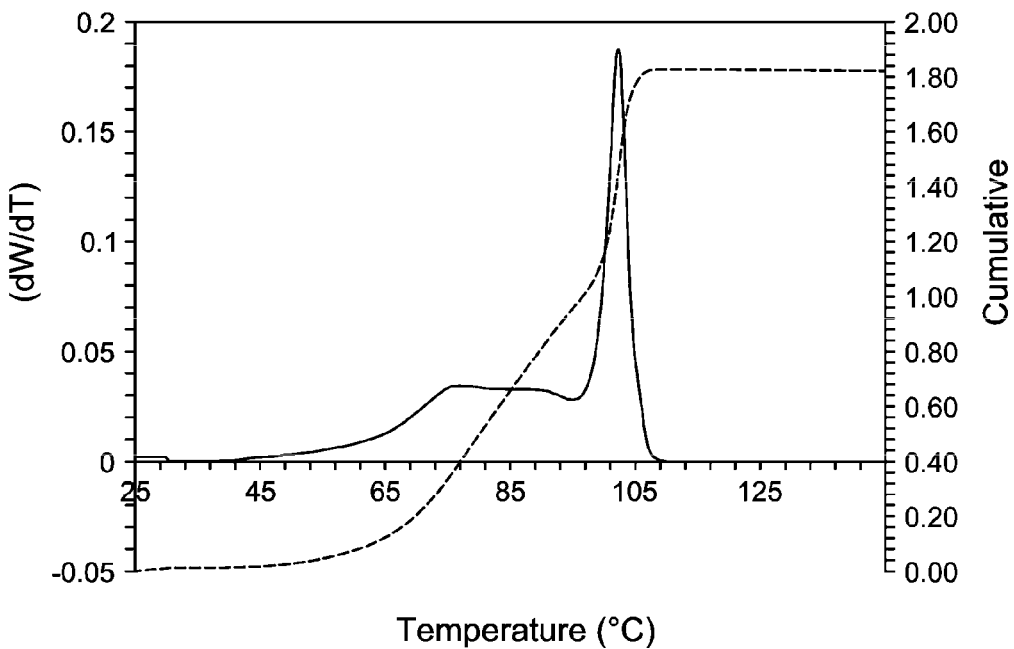
FIG. 2A shows the TREF trace for inventive resin 3-2.
Figure 2B:
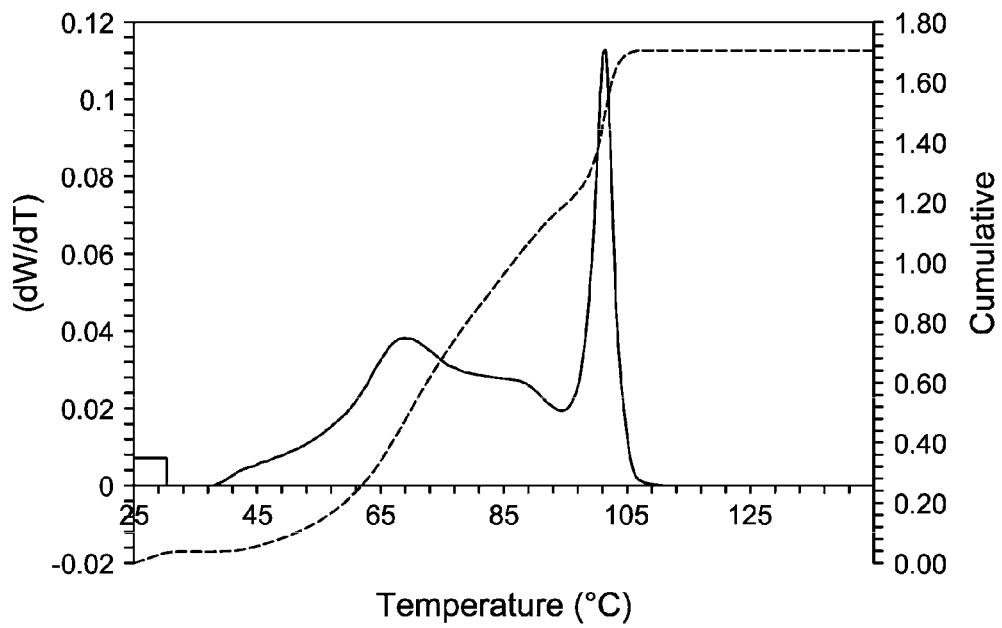
FIG. 2B shows the TREF trace for inventive resin 3-4.

Preferably, the inventive ethylene-based copolymer displays a high molecular weight "tail" or "bump" in dissolution temperatures. For example, an inventive ethylene-based copolymer that displays a first dissolution temperature and a second, higher dissolution temperature is considered to exhibit "bump" or "tail" in the dissolution temperatures (see FIGS. 2A and 2B). This is reflected in the ethylene-based copolymer having higher Mz and Mz/Mn values described above. Preferably, the inventive ethylene-based copolymers have an Mz value of greater than 250,000 g/mole or 300,000 g/mole or 350,000 g/mole, or 400,000 g/mole, or 450,000 g/mole, or within a range from 250,000 or 300,000 or 350,000 g/mole to 550,000 or 600,000 or 650,000 or 700,000 or 800,000 g/mole. Also, the inventive ethylene-based copolymers preferably have an Mz/Mn of greater than 8.0 or 9.0 or 10.0, or within a range of from 5.0 or 6.0 or 7.0 to 8.0 or 9.0 or 10.0 or 11.0 or 12.0 or 14.0 or 16.0 or 18.0

Preferably, the inventive ethylene-based copolymer has a $T_{90}$-$T_{10}$ value of 5° C. or greater, wherein $T_{10}$ is the temperature at which 10% of the eluted polymer is obtained, and $T_{90}$ is the temperature at which 90% of the eluted polymer is obtained in a TREF analysis, as described in Wild, et al., 20 J. POLY. SCI. POLY. PHYS. ED. 441 (1982). Preferably, at least one of $T_{10}$ or $T_{90}$ is in the range of from 45° C. to 85° C., and preferably $T_{90}$ is greater than 90° C.

Preferably, the inventive ethylene-based copolymer comprises branching that is reflective of the number of carbon atoms in the olefin used to copolymerize with the ethylene. This molecular architecture is in contrast to traditional LDPE resins for which the molecular structure is built upon the primary monomer, ethylene, coming together in any number of ways and number of repeating units determined by the amount, order and timing with which the ethylene monomer, initiator(s) and chain transfer agents are introduced into the reactors. The free radical chemistry leads to polymers with short chain branches (side groups) consisting of methyl, ethyl, propyl, butyl, pentyl, hexyl, etc. The ethylene-based copolymers of this invention have a much more ordered molecular architecture, wherein the only short chain branches observed are from the comonomer used, for example, a comonomer of 1-hexene ($C_6$) will typically produce butyl ($C_{6-2}=C_4$) short chain branches. Accordingly, if only 1-hexene is used as a comonomer, then only butyl side chains will be produced in the ethylene-based copolymer.

Most thermoplastic polyolefins display visco-elastic flow behavior and their viscosity decreases with increasing shear rate (also termed shear thinning). The inventive ethylene-based copolymers have good shear thinning. One way to quantify the shear thinning is to use a ratio of complex viscosity at a frequency of 0.01 rad/s to the complex viscosity at a frequency of 100 rad/s. Preferably, the complex viscosity ratio of the inventive ethylene-based copolymers produced herein is 50 or more, more preferably 100 or more, even more preferably 250 or more when the complex viscosity is measured at 190° C. The complex viscosity is measured at 190° C. over an angular frequency range from 0.01 to 100 rad/s using the procedure described below using Small Amplitude Oscillatory Shear (SAOS) testing. From the data generated by such a test, it is possible to determine the phase or loss angle δ, which is the inverse tangent of the ratio of G" (the loss modulus) to G' (the storage modulus). For a typical linear polymer, the loss angle at low frequencies (or long times) approaches 90° making the loss modulus much larger than the storage modulus. As frequencies increase, more of the chains relax too slowly to absorb energy during the oscillations, and the storage modulus grows relative to the loss modulus. Eventually, the storage and loss moduli become equal and the loss angle reaches 45°. In contrast, a branched chain polymer relaxes very slowly. Such branched polymers never reach a state where all its chains can relax during an oscillation, and the loss angle never reaches 90° even at the lowest frequency, ω, of the experiments. The loss angle is also relatively independent of the frequency of the oscillations in the SAOS experiment, another indication that the chains cannot relax on these timescales. In a plot of the phase angle δ versus the measurement frequency ω, polymers that have long chain branches exhibit a plateau in the function of δ(ω), whereas linear polymers do not have such a plateau. According to Garcia-Franco et al. (34(10) MACROMOLECULES 3115-3117 (2001)), the plateau in the aforementioned plot will shift to lower phase angles δ when the amount of long chain branching occurring in the polymer sample increases. SAOS data can be transformed into discrete relaxation spectra using the procedure in R. B. Bird, R. C. Armstrong, and O. Hassager, 1 DYNAMICS OF POLYMERIC LIQUIDS, FLUID MECHANICS, 273-275 ($2^{nd}$ Edition, John Wiley and Sons, 1987). The storage and loss moduli are simultaneously least squares fit with the functions: $G'(\omega_j)=\Sigma\eta_k\lambda_k\omega_j^2/(1+(\eta_k\omega_k)^2)$ $G''(\omega_j)=\Sigma\eta_k\lambda_k\omega_j/(1+(\eta_k\omega_k)^2)$ at the relaxation times $\lambda_k$=0.01, 0.1, 1, 10, and 100 seconds. The sums are from k=1 to k=5. The sum of the $\eta_k$'s is equal to the zero shear viscosity, $\eta_0$. Preferably of this invention, the inventive ethylene-based copolymer has a zero shear viscosity of 10,000 Pa·s or more, 15,000 Pa·s or more, 25,000 Pa·s or more; alternatively 80,000 Pa·s or less, 70,000 Pa·s or less or 50,000 Pa·s or less, as determined by small angle oscillatory shear analysis.

The inventive ethylene-based copolymers preferably have 0.10 or greater vinyl chain ends per 1000 carbon atoms, more preferably 0.15 or 0.20 or 0.25 or greater vinyl chain ends per 1000 carbon atoms. Some inventive ethylene-based copolymers have 0.05 or greater vinylidene chain ends per 1000 carbon atoms, more preferably 0.06 or 0.07 or 0.08 or greater vinylidene chain ends per 1000 carbon atoms. Most preferably, the ethylene-based copolymers have within the range from 0.10 or 0.15 to 0.40 or 0.50 terminal vinyl groups per 1000 carbons, and within a range from 0.06 or 0.07 to 0.11 or 0.12 or 0.12 vinylidene chain ends per 1000 carbon atoms.

Some inventive ethylene-based copolymers have greater than 35% vinyl chain ends (preferably greater than 40% vinyl chain ends, greater than 45% vinyl chain ends), based on the total number of unsaturations. The number of vinyl chain ends was determined using $^1$H NMR at 120° C. using deuterated tetrachloroethane as the solvent on an at least 250 MHz NMR spectrometer, and in selected cases, confirmed by $^{13}$C NMR. All spectra were recorded at 100° C. on a Bruker spectrometer operating at 500 MHz for proton and 125 MHz for carbon) for vinyl terminated propylene oligomers in 114 J. AM. CHEM. SOC. 1025-1032 (1992) that are useful herein. Allyl chain ends are reported as a molar percentage of the total number of moles of unsaturated groups (that is, the sum of allyl chain ends, vinylidene chain ends, vinylene chain ends, and the like).

The inventive ethylene-based copolymers have improved processability, whether used neat or as part of a blend with other polymers. In particular, markedly reduced motor load, reduced die pressure, reduced extruder head pressure, reduced torque, and reduced processing time are noted. These improved processability parameters are very important as they improve product output and reduce wear and tear on the film blowing line, thereby improving equipment lifetime and increasing the time period between repairs. Preferably, the extruder motor load is less than 70%, preferably less than 65%, or preferably less than 60% of the value when extruding commercial LLDPE having an $I_2$ of 1.0 g/10 min and density of 0.918 g/cm$^3$ (most desirably, Exceed™ 1018 metallocene polyethylene resins from ExxonMobil Chemical Company). Preferably, the extruder die pressure is less than 2500 psi, preferably less than 2400 psi, or preferably less than 2300 psi. Preferably, the extruder head pressure is less than 4000 psi, preferably less than 3750 psi, or preferably less than 3500 psi. Finally, the extruder torque is preferably less than 0.350 HP/rpm, preferably less than 0.325 HP/rpm or less than 0.315 HP/rpm.

The inventive ethylene-based copolymer may be used by itself as a polymer (neat) or it may be part of an in-reactor blend, or it may be blended as a modifier into a selected base polymer to form a physical blend.

Polymer Blends

The present invention also relates to polymer blends comprising the inventive ethylene-based copolymer. The polymer blend compositions may be in-reactor blends or homogeneous physical blends. "Homogeneous," as used herein, means free from visible gels. Preferably, the physical blends of this invention have less than 1 wt % of insoluble material, when the blend is dissolved in boiling xylenes.

The polymer blend compositions of this invention may comprise 0.5 wt % to 99.9 wt % of the inventive ethylene-based copolymer (preferably 1.0 wt % to 95 wt %, preferably 3 wt % to 75 wt %, preferably 5 wt % to 35 wt %, or preferably 5 wt % to 25 wt %). The remaining portion of the blend is preferably 0.1 wt % to 99.5 wt % of a polymer preferably selected from the group consisting of high density polyethylene, linear low density polyethylene, low density polyethylene, medium density polyethylene, and combinations thereof (preferably 5 wt % to 99 wt %, preferably 25 wt % to 97 wt %, preferably 65 wt % to 95 wt %, or preferably 75 wt % to 95 wt %). Examples of suitable polyethylenes include commercially available from ExxonMobil Chemical Company in Baytown, Tex. under the tradenames Exceed™, Enable™, and Exact™, as well as the Engage™ polymers available from DuPont/Dow.

The Enable products, some of which are used herein as comparative examples, are made using a metallocene catalyst and the products have a small amount of long chain branching in them. The Enable products do not perform as well as the inventive ethylene-based polymers.

Optionally, the polymer blend composition may also include one or more polymer "additives", such as reinforcing and non-reinforcing fillers, scratch resistant agents, plasticizers, antioxidants, heat stabilizers, extender oils, lubricants, antiblocking agents, antistatic agents, anti-fogging agent, waxes, foaming agents, pigments, flame/fire retardants, dyes and colorants, ultraviolet absorbers, and nano-fillers. Other additives include, for example, blowing agents, processing aids, tackifying resins, and other processing aids known in the polymer compounding art. The lists described herein are not intended to be inclusive of all types of additives which can be employed with the present invention. Upon reading this disclosure, those of skilled in the art will appreciate other additives can be employed to enhance properties. As is understood by the skilled in the art, the blends of the present invention can be modified to adjust the characteristics of the blends as desired. The aforementioned additives can be either added independently or incorporated into an additive or masterbatch. Such additives can comprise up to 70 wt %, more preferably up to 65 wt %, of the total additive or masterbatch composition.

Also, optionally, the polymer blend composition may include one or more slip agents or mold-release agents to facilitate moldability, preferably present at 50 ppm to 10 wt %, more preferably 50 ppm to 5000 ppm, even more preferably 0.01 wt % to 0.5 wt % (100 ppm to 5000 ppm), even more preferably 0.1 wt % to 0.3 wt % (1000 ppm to 3000 ppm), based upon the weight of the composition. Desirable slip additives include but are not limited to saturated fatty acid amides (such as palmitamide, stearamide, arachidamide, behenamide, stearyl stearamide, palmityl pamitamide, and stearyl arachidamide); saturated ethylene-bis-amides (such as stearamido-ethyl-stearamide, stearamido-ethyl-palmitamide, and palmitamido-ethyl-stearamide); unsaturated fatty acid amides (such as oleamide, erucamide, and linoleamide); unsaturated ethylene-bis-amides (such as ethylene-bis-stearamide, ethylene-bis-oleamide, stearyl-erucamide, erucamido-ethyl-erucamide, oleamido-ethyl-oleamide, erucamido-ethyl-oleamide, oleamido-ethyl-lerucamide, stearamido-ethyl-erucamide, erucamido-ethyl-palmitamide, and palmitamido-ethyl-oleamide); glycols; polyether polyols (such as Carbowax); acids of aliphatic hydrocarbons (such as adipic acid and sebacic acid); esters of aromatic or aliphatic hydrocarbons (such as glycerol monostearate and pentaerythritol monooleate); styrene-alpha-methyl styrene; fluoro-containing polymers (such as polytetrafluoroethylene, fluorine oils, and fluorine waxes); silicon compounds (such as silanes and silicone polymers, including silicone oils, modified silicones, and cured silicones); sodium alkylsulfates, alkyl phosphoric acid esters; stearates (such as zinc stearate); and mixtures thereof.

Inventive Films

This invention also relates to films comprising (or consisting essentially of, or consisting of) the inventive ethylene-based copolymers or the polymer blend compositions described herein. The inventive ethylene-based copolymers and polymer blend compositions disclosed herein may be utilized to prepare monolayer films or multilayer films. These films may be formed by any number of well-known extrusion or coextrusion techniques discussed below. Films may be unoriented, uniaxially oriented or biaxially oriented. Physical properties of the film may vary depending on the film forming techniques used.

Preferably, films containing the ethylene-based copolymer and polymer blend compositions, monolayer or multilayer, may be formed by using casting techniques, such as a chill roll casting process. Such chill roll casting processes and apparatus are well known in the art, and are described, for example, in The Wiley-Encyclopedia of Packaging Technology, Second Edition, A. L. Brody and K. S. Marsh, Ed., John Wiley and Sons, Inc., New York (1997). Although chill roll casting is one example, other forms of casting may be employed.

More preferably, films containing the inventive ethylene-based copolymers and polymer blend compositions, monolayer or multilayer, may be formed using blown techniques, i.e., to form a blown film. For example, the composition can be extruded in a molten state through an annular die and then blown and cooled to form a tubular, blown film, which can then be axially slit and unfolded to form a flat film. As a specific example, blown films can be prepared as follows. The polymer blend composition is introduced into the feed hopper of an extruder, such as a 63.5 mm Egan extruder that is water-cooled, resistance heated, and has a L/D ratio of 24:1. The film can be produced using a 15.24 cm Sano die with a 2.24 mm die gap, along with a Sano dual orifice non-rotating, non-adjustable air ring. The film is extruded through the die into a film cooled by blowing air onto the surface of the film. The film is drawn from the die typically forming a cylindrical tube of film that is cooled, collapsed and, optionally, subjected to a desired auxiliary process, such as slitting, treating, sealing, or printing. Typical melt temperatures are from 175° C. to 225° C. Blown film rates are generally from 5 to 30 lbs per hour per inch of die circumference. The finished film can be wound into rolls for later processing, or can be fed into a bag machine and converted into bags. An example of a blown film process and apparatus suitable for forming films according to U.S. Pat. No. 5,569,693. Of course, other blown film forming methods can also be used.

Physical properties of the film can vary from those of the polymer or polymer blend, depending on the film forming techniques used. The films can be of any desirable thickness or composition, but most preferably within a range from 1 or 5 or 10 or 20 microns to 30 or 50 or 100 or 200 or 300 microns. The resins used to make the films can be blended with other additives such as pigments, antioxidants, fillers, etc., as is known in the art, as long as they do not interfere with the desired film properties. The films of the present invention have a combination of unique and useful properties as described in more detail below. When the blends "consist essentially of" the ethylene-based copolymers and other polyethylenes (e.g., LLDPE, HDPE, etc), what is meant is that the "additives" are present at a level of less than 5 wt % of the blend.

Most preferably, this invention relates to a film comprising, for example, at least 5 wt % of the inventive ethylene-based copolymer comprising for example from 75.0 wt % to 99.5 wt % of ethylene-derived units and 0.5 wt % to 25.0 wt % of $C_3$ to $C_{20}$ olefin derived units, where the inventive ethylene-based copolymers have, for example, a density in the range of from 0.900 or 0.920 g/cm$^3$ to less than 0.950 g/cm$^3$; a g'(vis) of less than 0.80; a melt index, $I_2$, of from 0.25 to 1.5 g/10 min; a Mw/Mn within a range from 3.0 to 6.0; a Mz/Mn of greater than 8.0; an absence of a local minimum loss angle at a complex modulus, G*, of 1.00×10$^4$ to 3.00×10$^4$ Pa; and wherein the film has for example (a) a 1% Secant Modulus MD of 30,000 psi or greater; (b) an Elmendorf Tear MD value of 100 g/mil or greater; and (c) a Dart Impact of 225 g/mil or greater.

As a blend, the inventive films comprise at least 5 wt % of the inventive ethylene-based copolymer described herein, and preferably greater than 8 wt % or 10 wt % or 12 wt % or 15 wt % or 18 wt % or 20 wt % or 25 wt %; alternately the inventive films comprise the ethylene-based copolymers at a level of less than 35 wt % or 30 wt % or 25 wt %. The balance of the film may comprise other polyethylenes, which may be homopolymers or copolymers, for example, a VLDPE, a LDPE (such as a "high pressure" derived LDPE, or "HD-LDPE", or just "LD"), a LLDPE, a MDPE, a HDPE, or a DPE, as well as other polyethylenes known in the art. The polyethylene can be produced by any suitable process, including metallocene-catalyzed processes and Ziegler-Natta catalyzed processes. Further, each layer can be a blend of two or more such polyethylenes, and can include additives known in the art. Further, one skilled in the art will understand that the layers of a multilayer film preferably have the appropriate viscosity match.

Preferably, the film is a blown film. The film may be a monolayer or multilayer film, and the inventive ethylene-based copolymers described herein may be in multiple layers.

The inventive films have a good balance of stiffness versus toughness as indicated by machine direction tear strength (MD Elmendorf Tear), 1% Secant Modulus (MD), and dart drop impact strength performance (Dart Impact). Desirably, the films exhibit the relationship of having a Dart Drop (g/mil) of greater than −8.09×[Average Elmendorf Tear (g/mil)]+853.81. Also the films preferably exhibit the relationship of having a Tensile Strength at Yield of greater than 4.274×[Elmendorf Tear (g/mil)]+300, such as demonstrated by the data in FIG. 16A.

The films may desirably have a 1% Secant Modulus in the machine direction (1% Secant Modulus MD), reported in pounds per square inch (psi), measured according to ASTM D882-95a, of 30,00 or 40,000 or 50,000 or 60,000 psi or greater, or preferably within a range from 30,000 or 50,000 or 60,000 psi to 100,000 or 120,000 or 140,000 psi.

The films may desirably have a MD Elmendorf Tear, as measured by ASTM D1922-94, of 100 g/mil or greater. Preferably, the films can have a MD Elmendorf Tear of 100 g/mil to 450 g/mil. Preferably, the MD Elmendorf Tear can range from a low of 110 g/mil, 120 g/mil, or 150 g/mil to a high of 425 g/mil, 400 g/mil, or 375 g/mil.

The films may desirably have a Dart Impact (Method A), as measured according to ASTM D1709-91, of 225 g/mil to 450 g/mil (preferably 250 g/mil to 450 g/mil; preferably 275 g/mil to 440 g/mil). The film may comprises 25 wt % or more of the inventive ethylene-based copolymer and has a Dart Impact of 320 g/mil or greater (340 g/mil or greater, 350 g/mil or greater, 360 g/mil or greater).

The films may desirably have a total haze, as measured according to ASTM D1003-95, of 0.2 wt % to 30%. Preferably, the films have a haze of less than 25%; less than 20%; less than 15%; or less than 10%. Preferably, the haze can range from a low of 2%, 4%, or 5% to a high of 10%, 15%, or 25%.

The films may desirably have an internal haze, as measured according to ASTM D1003-95, of 0.2% to 5%. Preferably, the films have an internal haze of less than 5%; less than 4%; less than 3%; or less than 1.5%. Preferably, the haze can range from a low of 0.2%, 0.75%, or 1.0% to a high of 2%, 4%, or 5%. Internal haze is the haze excluding any film surface contribution. The film surfaces are coated with ASTM approved inert liquids to eliminate any haze contribution from the film surface topology. The haze measurement procedure is per ASTM D 1003.

The films may desirably have a Gloss 45° MD, as measured according to ASTM D2457-90, of 45 to 75. The Gloss 45° MD may range from a low of 45, 50, or 55 to a high of 60, 65, or 75.

The films have a desirable "drawability", which is the melt strength of the polymer used to make the blown film and is the ratio of the die gap to film gauge after the polymer is drawn out into a film. A higher drawability or "Draw" is desirable. Preferably, the total draw of the inventive films is 40 or greater, preferably 45 or greater, preferably 50 or greater, preferably 60 or greater, or preferably 70 or greater.

Additionally, films containing the ethylene-based copolymers and blends described herein have improved seal strength and hot tack performance. Preferably, a film comprising 25 wt % or more of the inventive ethylene-based copolymer and has a seal strength of at least 2.0 lbs/in (357 g/cm) at a seal initiation temperature of 105° C. The films preferably have a seal initiation temperature so that it is suitable for packaging applications, such as food packaging. The desired seal initiation temperature ("SIT") may depend on the end use application of the film, for example, for chocolate bars the SIT may be the temperature at which the seal strength is 200 g/inch (80 g/cm), for potato chips in the United States the desired SIT may be the temperature at which the seal strength is 500 g/inch (20 g/cm), and for potato chips in Asia the SIT may be the temperature at which the seal strength is 1000 g/inch (400 g/cm). The SIT may also depend on the type of seal used, for example, a fin seal as compared to a crimp seal.

The films preferably have a hot tack strength of greater than 320 g/inch (126 g/cm) (preferably greater than 340 g/inch (134 g/cm), greater than 360 g/inch (142 g/cm), greater than 380 g/inch (150 g/cm), greater than 400 g/inch (157 g/cm), or greater than 410 g/inch (162 g/cm)). "Hot tack" is the strength of a heat seal immediately after sealing, while still in a hot condition, that is, before it has cooled down to ambient temperature and achieved its final strength. In production lines, the package is often filled by dropping the product into the package from a certain height, or by horizontally filling, both of which will exert a force on the package bottom. If the package bottom cannot resist the disruptive force of filling, the seal on the bottom of the package will fail. For optimum production line efficiency, the interval between heat-sealing the film to make the package and filling the package with product is very short, and it is usually not possible for seal completely cool before filling. Accordingly, hot tack strength becomes important.

The films possess an excellent balance of mechanical properties, toughness, sealability and cling/adhesive properties. As such, the films can be used in hot fill applications or packaging materials heated at temperatures up to 260° F. (126° C.) during packaging, such as cement, sand, salt, and retort bag applications such as pouches, bags and sacks containing consumer products including food. The films can also be used for shrink films and form fill and seal applications requiring abuse resistance. The films also possess good softness/feel and optical/clarity properties useful for food packaging at any temperature.

In addition to films, the resin blends described herein will find utility in other applications like, but not limited to: extrusion coating, injection molding, rotomolding, and blow molding applications.

The various descriptive elements and numerical ranges disclosed herein for the inventive ethylene-based copolymer and films can be combined with other descriptive elements and numerical ranges to describe the invention; further, for a given element, any upper numerical limit can be combined with any lower numerical limit described herein. The features of the invention are demonstrated in the following non-limiting examples.

EXAMPLES

Tests and Materials

The properties cited below were determined in accordance with the following test procedures. Where any of these properties is referenced in the appended claims, it is to be measured in accordance with the specified test procedure. Where applicable, the properties and descriptions below are intended to encompass measurements in both the machine and transverse directions. Such measurements are reported separately, with the designation "MD" indicating a measurement in the machine direction, and "TD" indicating a measurement in the transverse direction.

Gauge, reported in mils, was measured using a Measuretech Series 200 instrument. The instrument measures film thickness using a capacitance gauge. For each film sample, ten film thickness datapoints were measured per inch of film as the film was passed through the gauge in a transverse direction. From these measurements, an average gauge measurement was determined and reported.

Elmendorf tear (tear) was measured as specified by ASTM D-1922.

Tensile properties, including tensile strength, tensile stress, ultimate tensile stress, tensile strain, ultimate tensile strain, tensile stress at 100% (200%, 300%, 400%, 500%, 600%, 700%, 800%, etc.) elongation, stress and strain at the primary yield point, stress and strain at the secondary yield point, 1% and 2% Secant modulus, tensile strength at yield, tensile strength at break, ultimate tensile strength, elongation at yield, elongation at break, yield stress, and strain hardening were measured as specified by ASTM D-882.

Melt index (MI) and high load melt index (HLMI) were determined according to ASTM 1238 (190° C., 2.16 ($I_2$) or 21.6 kg ($I_{21}$), respectively). Melt index ratio (MIR) was determined according to ASTM 1238 and is the ratio of HLMI to MI (e.g., $I_{21}/I_2$). In the event a weight is not specified as part of a melt index, it is assumed that 2.16 kg was used.

Density was determined measured as specified by ASTM D-1505 using chips cut from plaques compression molded in accordance with ASTM D-4703-07, aged in for 40 hrs at 23° C. plus or minus 2° C., unless specifically stated otherwise.

Dart Impact (also known as Dart $F_{50}$, or Dart Drop Impact or Dart Drop Impact Strength) was measured as specified by ASTM D-1709, method A.

Haze (both internal and total) reported as a percentage (%), was measured as specified by ASTM D-1003.

Gloss, a dimensionless number, was measured as specified by ASTM D-2457 at 45°.

Melting point temperature was measured using the DSC procedure as follows: Samples weighing approximately 5 to 10 mg were sealed in aluminum sample pans. The DSC data were recorded by first cooling the sample to −50° C. and then gradually heating it to 200° C. at a rate of 10° C./minute. The sample was kept at 200° C. for 5 minutes before a second cooling-heating cycle was applied. Both the first and second cycle thermal events were recorded. The melting temperature (Tm) was measured and reported during the second heating cycle (or second melt).

Molecular weight distribution (polydispersity) is Mw/Mn. Measurements of weight average molecular weight ($M_w$), number average molecular weight ($M_n$), and z-average molecular weight (Mz) were determined by Gel Permeation Chromatography as described in 34(19) MACROMOLECULES 6812 (2001), which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument was operated with a flow rate of 1.0 cm³/min, and an injection volume of 300 µL. The various transfer lines, columns and differential refractometer (the DRI detector) were housed in an oven maintained at 145° C. Polymer solutions were prepared by heating 0.75 to 1.5 mg/mL of polymer in filtered 1,2,4-Trichlorobenzene (TCB) containing about 1000 ppm of BHT at 160° C. for 2 hours with continuous agitation. A sample of the polymer containing solution was injected into the GPC and eluted using filtered 1,2,4-Trichlorobenzene (TCB) containing ~1000 ppm of BHT. The separation efficiency of the column set was calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000,000 g/mole, were used to generate the calibration curve. The flow rate was calibrated for each run to give a common peak position for a flow rate marker (taken to be the positive inject peak) before determining the retention volume for each polystyrene standard. The flow marker peak position was used to correct the flow rate when analyzing samples. A calibration curve (log (Mp) vs. retention volume) was generated by recording the retention volume at the peak in the DRI signal for each PS standard, and fitting this data set to a 2nd-order polynomial. The equivalent polyethylene molecular weights were determined by using the Mark-Houwink coefficients shown wherein k is $5.79 \times 10^{-4}$ dL/g and "A" is 0.695, both for polyethylene.

¹H NMR data for polymer characterization (such as vinyls/ 1000 C. etc.) was collected at 120° C. in a 5 mm probe using a Varian Spectrometer with a ¹Hydrogen frequency of 400 MHz. The data was recorded using a maximum pulse width of 45°, 8 seconds between pulses, and signal averaging 120 transients in solvent of $C_2D_2Cl_4$.

The dynamic shear viscosity (or complex viscosity) as a function of frequency is determined by small-amplitude oscillatory shear (SAOS) rheology, as described above.

Some commercially available polymers were used as comparative examples and are shown in Table 1, below.

TABLE 1

| Polymer | Source | Properties |
|---------|--------|------------|
| Exceed™ 1018 | ExxonMobil Chemical Company (Houston, TX) | Ethylene-hexene copolymer; density = 0.918 g/cm³; MI (190° C./2.16 kg) = 1 g/10 min., Tm = 119° C. |
| ExxonMobil™ LDPE LD 071 | ExxonMobil Chemical Company (Houston, TX) | density = 0.924 g/cm³; MFR (190° C./2.16 kg) = 0.70 g/10 min. |
| ExxonMoil™ LDPE LD 051 | ExxonMobil Chemical Company (Houston, TX) | density = 0.919 g/cm³; MI (190° C./2.16 kg) = 0.25 g/10 min.; Tm = 230° F. |
| Enable™ 20-10 | ExxonMobil Chemical Company (Houston, TX) | Ethylene-hexene copolymer; density = 0.920 g/cm³; MI (190° C./2.16 kg) = 1 g/10 min.; Tm = 237° F. |
| Enable™ 35-05 | ExxonMobil Chemical Company (Houston, TX) | Ethylene-hexene copolymer; density = 0.935 g/cm³; MI (190° C./2.16 kg) = 0.5 g/10 min.; Tm = 254° F. |

Example 1

Production of Polyethylene Resins 3-2, 3-3, & 3-4

Polymerization:

Ethylene-hexene copolymer was made by reacting ethylene with hexene using silica supported dimethylsilylene(2,3,4,5-tetramethyl-1-cyclopentadienyl)(3-phenyl-1-indenyl) zirconium dichloride (Supported Metallocene I) activated with MAO. Three yields were collected under slightly different polymerization conditions (resins 3-2, 3-3, & 3-4).

Supported Metallocene I Preparation: Silica Supported Dimethylsilylene(2,3,4,5-tetramethyl-1-cyclopentadienyl)(3-phenyl-1-indenyl)zirconium dichloride Preparation of dimethyl(3-phenyl-1H-indenyl)(2,3,4,5-tetramethylcyclopentadienyl)silane (Compound A)

To a solution of chlorodimethyl(2,3,4,5-tetramethylcyclopenta-2,4-dien-1-yl)silane (5.00 g, 23.3 mmol, 1.00 eq.) in ether (25 mL) at −35° C. was added lithium(1-phenylindenide) (4.85 g, 24.5 mmol, 1.05 eq.). The reaction was stirred for 23 hours, and the volatiles were then removed under vacuum. The residue was extracted with pentane (40 mL) and the extract was filtered. The resulting solution was evaporated under vacuum to give a thick oil. Yield 7.07 g (82%). ¹H NMR ($C_6D_6$): δ 7.74 (d, 1H), 7.65 (d, 2H), 7.48 (d, 1H), 7.25 (m, 5H), 6.60 (s, 1H), 3.69, (s, 1H), 2.92 (br s, 1H), 1.93 (s, 3H), 1.90 (s, 3H), 1.82 (s, 3H), 1.821 (s, 3H), −0.09 (s, 3H), −0.39 (s, 3H).

Preparation of dilithium[tetramethylcyclopentadien-idedimethylsilyl(3-phenylindenide) 1.10 etherate (Compound B)

To a solution of dimethyl(3-phenyl-1H-indenyl)(2,3,4,5-tetramethylcyclopentadienyl)silane (Compound A, 7.03 g, 19.0 mmol, 1.00 eq.) in ether (25 mL) at −35° C. was added 2.63M butyllithium in hexanes (14.8 mL, 38.9 mmol, 2.05 eq.). The reaction was stirred for 20 hours and then filtered to give a solid. The solid was washed with pentane (2×40 mL) and dried under vacuum. Yield 8.51 g (97%). $^1$H NMR (THF-d8): δ 7.70 (d, 1H), 7.54 (m, 3H), 7.12 (s, 1H), 7.03 (t, 2H), 6.57 (t, 1H), 6.48, (t, 1H), 6.43 (t, 1H), 3.39 (q, 4.4H), 2.20 (s, 6H), 1.91 (s, 6H), 1.13 (t, 6.5H), 0.64 (br s, 6H).

Preparation of dimethylsilylene(2,3,4,5-tetramethyl-1-cyclopentadienyl)(3-phenyl-1-indenyl)zirconium dichloride (Metallocene I)

To a suspension of zirconium tetrachloride bis(etherate) (2.00 g, 5.25 mmol, 1.00 eq.) in ether (25 mL) at −35° C. was added dilithium[tetramethylcyclopentadienidedimethylsilyl (3-phenylindenide) 1.10 etherate (Compound B, 2.43 g, 5.24 mmol, 1.00 eq.). The reaction was stirred for 16 hours and was then evaporated under vacuum, leaving a solid. The solid was extracted with dichloromethane (50 mL, then 3×10 mL) and the extracts were filtered. The resulting solution was evaporated under vacuum to yield a solid. The solid was washed with pentane (2×20 mL) and dried under vacuum. Yield 2.53 g (91%). $^1$H NMR (CD$_2$Cl$_2$): δ 7.90. (d, 1H), 7.60 (m, 3H), 7.49 (t, 2H), 7.38 (m, 2H), 7.10 (m, 1H), 6.00 (s, 1H), 2.00 (s, 3H), 1.96 (s, 3H), 1.92 (s, 3H), 1.89 (s, 3H), 1.23 (s, 3H), 1.00 (s, 3H).

Supported dimethylsilylene(2,3,4,5-tetramethyl-1-cyclopentadienyl(3-phenyl-1-indenyl)zirconium dichloride (Supported Metallocene I)

30 wt % MAO in toluene (Albemarle, Baton Rouge, La., 6.25 g, 32.3 mmol, 120 eq.) and toluene (6.50 g) were combined and stirred for 15 minutes to give a clear solution. To this MAO solution was added dimethylsilylene(2,3,4,5-tetramethyl-1-cyclopentadienyl)(3-phenyl-1-indenyl)zirconium dichloride (Metallocene I, 0.147 g, 0.27 mmol, 1.00 eq.). The reaction was stirred for 15 minutes and then DAVISON™ 948 silica (5.00 g, dried at 600° C. for 16 hours) was added. The slurry was mixed for 10 minutes and then dried under vacuum for 22 hours. Yield 6.87 g (98%). The supported catalysts were then injected with nitrogen into the polymerization reactor as described below.

Polymerization Methods

The polymerization was conducted in a laboratory gas phase reactor having a fluidized bed reactor equipped with devices for temperature control, catalyst feeding or injection equipment, gas chromatograph analyzer for monitoring and controlling monomer and gas feeds, and equipment for polymer sampling and collecting. The reactor consisted of a 6" (15.24 mm) diameter bed section increasing to 10" (25.4 mm) at the reactor top. Gas came in through a perforated distributor plate allowing fluidization of the bed contents and polymer sample was discharged at the reactor top.

TABLE 2

Reactor Conditions

| | Resin | | |
|---|---|---|---|
| | 3-2 | 3-3 | 3-4 |
| | | Catalyst | |
| | Supported Metallocene I | Supported Metallocene I | Supported Metallocene I |
| Temperature, ° F. (° C.) | 167 (75) | 176 (80) | 176 (80) |
| Hexene (mol %) | 2.1 | 2.31 | 2.31 |
| Ethylene (mol %) | 70 | 70 | 70 |
| Hydrogen (ppm) | 50 | 100 | 100 |
| Hydrogen/Ethylene Ratio (ppm/%) | 0.7 | 1.4 | 1.4 |

Productivity was 7,000 lbs resin/lb of catalyst and the production rate was 50 lbs of resin per hour.

Polymer Characterization

The ethylene copolymers produced (Resins 3-2, 3-3, and 3-4) were analyzed for selected physical properties as reported in Table 3.

TABLE 3

| | Inventive | | | Comparataive |
|---|---|---|---|---|
| Properties | 3-2 | 3-3 | 3-4 | Exceed™ 1018 |
| MI or I$_2$ (g/10 min.) | 0.437 | 1.1 | 1.2 | 1.0 |
| Density (g/cm$^3$) | 0.926 | 0.919 | 0.92 | 0.918 |
| Vinyls/1000 C. | 0.27 | 0.29 | 0.35 | 0.03 |
| Vinylenes/1000 C. | 0.09 | 0.08 | 0.14 | 0.06 |
| Vinylidenes/1000 C. | 0.08 | 0.08 | 0.10 | 0.03 |
| Tri-substituted/1000 C. | 0.13 | 0.06 | 0.12 | 0.10 |
| Mn (g/mol) | 37,390 | 29,858 | 28,887 | 37,567 |
| Mw (g/mol) | 133,792 | 116,074 | 115,809 | 109,001 |
| Mz (g/mol) | 406,824 | 346,471 | 356,021 | 249,041 |
| Mw/Mn | 4.13 | 3.89 | 4.01 | 2.9 |
| g' (vis) | 0.723 | 0.688 | 0.706 | 0.84 |
| g' (z avg) | 0.571 | 0.529 | 0.546 | >0.8 |

FIG. 1 shows the GPC chromatogram of the inventive resin 3-2 compared with the comparative resins of Table 1. The molar mass distribution of the inventive resin 3-2 is different from that in Exceed™ 1018, Enable™ 20-10, and the LDPE (LD 071) resins, as shown in FIG. 1. The inventive resin 3-2 has less lower molecular weight material than Enable™ 20-10 and LDPE LD 071 resins. The inventive resin 3-2 also has more lower molecular weight material than Exceed™ 1018 resin and more higher molecular weight material than Exceed™ 1018, Enable™ 20-10 and 35-05, and LDPE LD 071 resins.

TREF

The inventive resins 3-2 and 3-4 exhibited multimodality in the TREF traces (see FIGS. 2A and 2B, respectively), showing a lower melting component having a melting point less than 90° C. and a higher melting component having a melting point greater than 90° C.

SAOS (Small-Amplitude Oscillatory Shear)

Figure 3A:
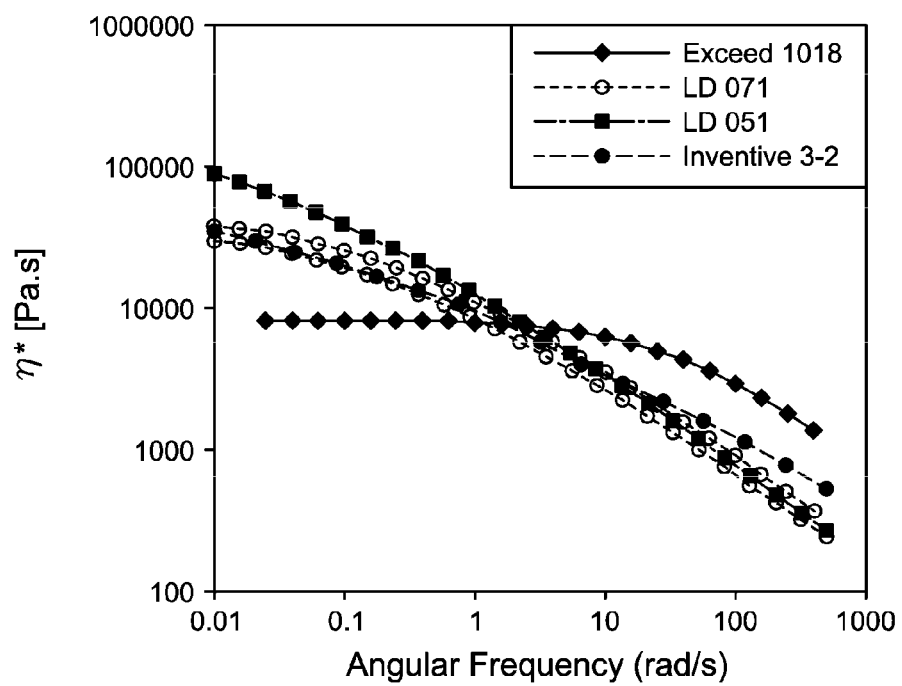
FIG. 3A shows the comparison of inventive resin 3-2 to comparative commercial resins by SAOS.
Figure 3B:
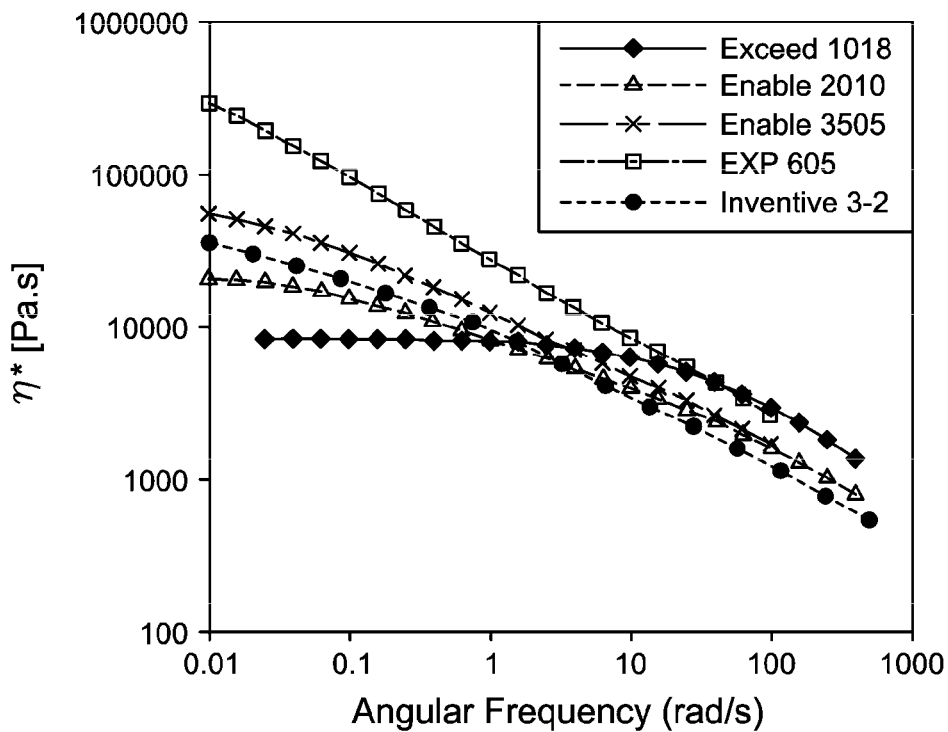
FIG. 3B shows the comparison of inventive resin 3-2 to comparative commercial resins by SAOS.
Figure 3C:
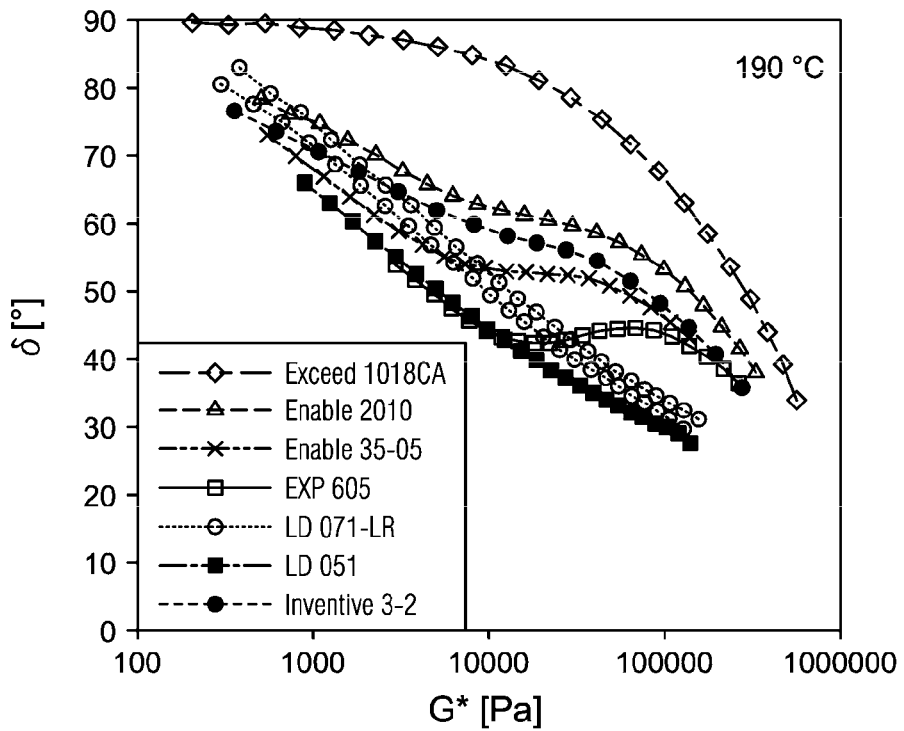
FIG. 3C shows the comparison of inventive resin 3-2 to comparative commercial resins by a Van Gurp-Palmen treatment.

The ethylene-hexene copolymers were compared to several commercially available ethylene by SAOS (see FIGS. 3A and 3B). The SAOS viscosity of the ethylene-hexene copolymers from Run #3-2 is similar to that of ExxonMobil™ LDPE LD 071, Enable™ 20-10 polyethylene, and Enable™ 35-05 polyethylene. Additionally, the zero shear viscosity of the ethylene-hexene copolymer 3-2 is less than that of ExxonMobil™ LDPE LD 051.

The SAOS analysis of the ethylene-hexene copolymer 3-2 revealed a complex composition, which may be bimodal. The inventors suggest that a second component may add a new dimension to expected melt strength, elongational viscosity, and bubble stability. Indeed, the ethylene-hexene copolymer 3-2 is comparable to Enable™ polyethylene resins and is markedly different from LDPE resins (LDPE LD 071 and LDPE LD 051) (see FIG. 3C).

Capillary Rheometry

Figure 4A:
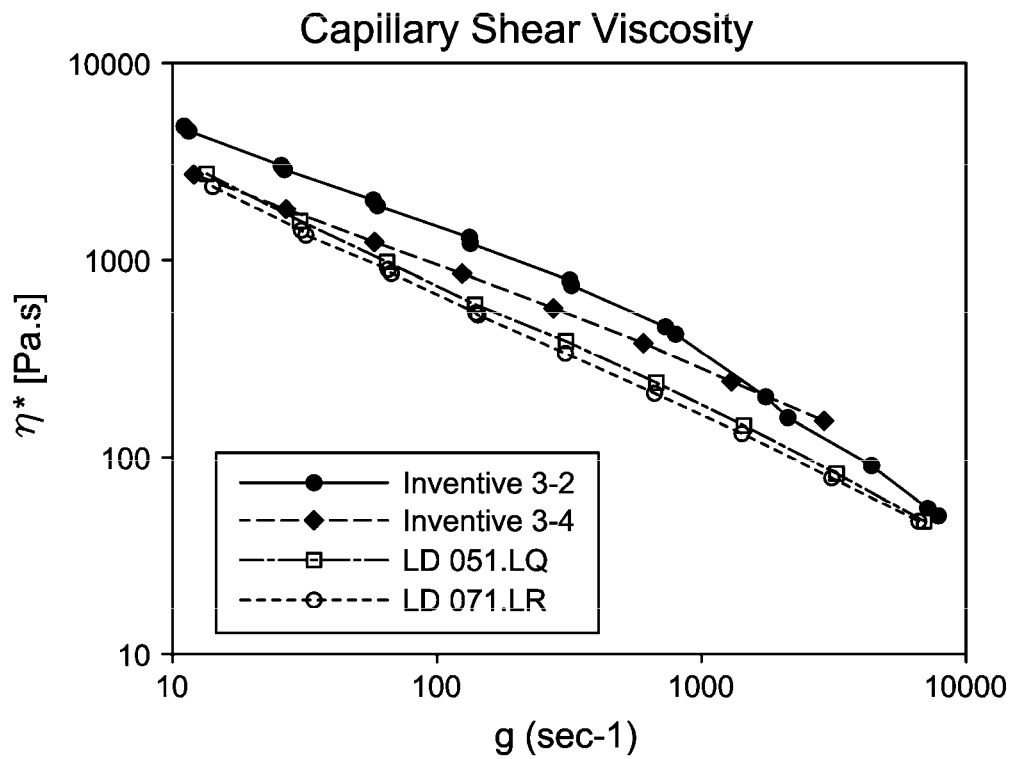
FIG. 4A shows the comparison of the viscosity of the inventive resins 3-2 and 3-4 to comparative commercial LDPE resins.

The viscosity of the ethylene-hexene copolymer resin 3-2 exceeds that of the comparative LDPE resins (LDPE LD 051 and LDPE LD 071), as shown in FIG. 4A. The viscosity of the ethylene-hexene copolymers from Run number 3-4 is also greater than that of the comparative LDPE resins, as seen in FIG. 4A.

Figure 4B:
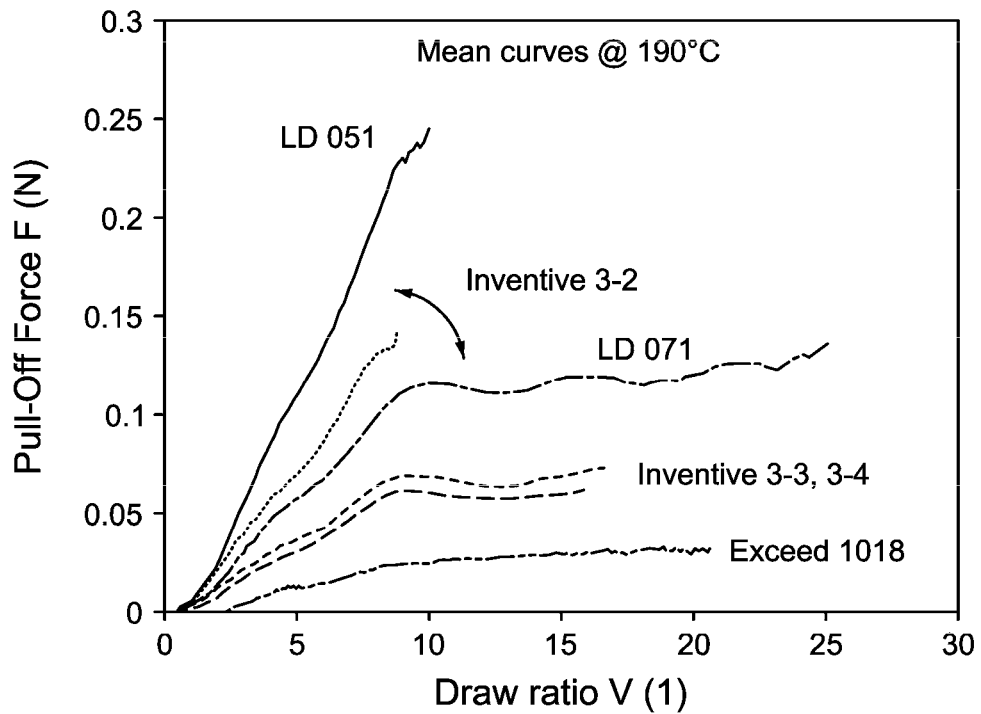
FIG. 4B shows the comparison of the melt strength of the inventive resins 3-2, 3-3 and 3-4 to comparative commercial resins.
Figure 4C:
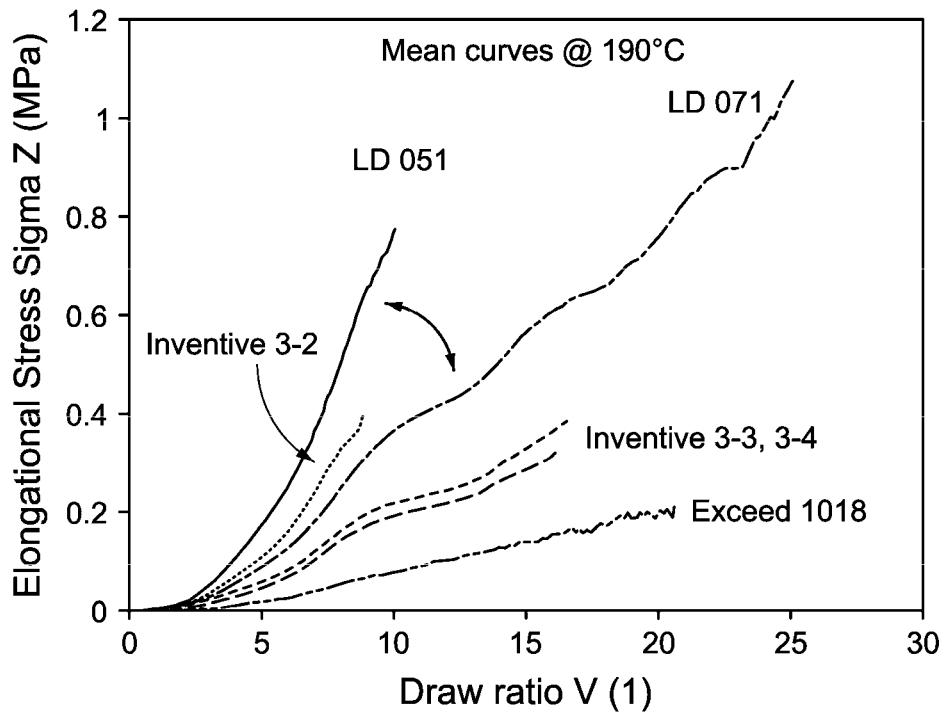
FIG. 4C shows the comparison of the elongational viscosity of the inventive resins 3-2, 3-3 and 3-4 to comparative commercial resins.

FIGS. 4B and 4C show that the ethylene-hexene copolymer resin 3-2 has a melt strength greater than those of LDPE LD 071, but less than that of LDPE LD 051. Additionally, the ethylene-hexene copolymer resins 3-3 and 3-4 have a melt strength and elongational viscosity less than that of the comparative LDPE resins.

Polymer Compounding

The ethylene-hexene copolymers listed in Table 3 were stabilized with an additive package comprising 500 ppm Irganox 1076, 1000 ppm Irgafos 168, 800 ppm Dynamar FX-5920A, and compounded using an Werner Pfeliderer ZSK-57 extruder equipped with a 20\60\80\20 screen pack and operated using counter rotating intermeshing twin screws operated under the conditions shown in Table 4.

TABLE 4

Extrusion Conditions used to compound ethylene-hexene copolymers with additives

| | Resin | | |
|---|---|---|---|
| | 3-2 | 3-3 | 3-4 |
| Start Time | 13:49:57 | 6:04:21 | 10:16:01 |
| End Time | 17:04:41 | 10:01:10 | 13:50:04 |
| Sample Produced (lbs) | 602 | 762 | 682 |
| Nitrogen Setting (SCF/hr) | 12 | 12 | 12 |
| Production Rate (lbs/hr) | 180 | 180 | 180 |
| Screw Speed (RPM) | 180.67 | 180.87 | 141.01 |
| Screen Pressure (psi) | 450.9 | 331.5 | 329.98 |
| Melt temp (° F.) | 430.27 | 400.26 | 398.91 |
| Extruder Temperature (° F.) | | | |
| Zone 1 | 338.2 | 338.0 | 337.8 |
| Zone 2 | 275.5 | 288.1 | 287.8 |
| Zone 3 | 314.6 | 330.4 | 331.4 |
| Zone 4 | 325.8 | 338.4 | 340.6 |
| Zone 5 | 338.5 | 339.6 | 338.3 |
| Zone 6 | 372.4 | 357.0 | 351.2 |
| Zone 7 | 424.3 | 389.3 | 388.5 |
| Zone 8 | 382.7 | 403.1 | 389.2 |
| Zone 9 | 380.4 | 380.1 | 383.0 |

TABLE 4-continued

Extrusion Conditions used to compound ethylene-hexene copolymers with additives

| | Resin | | |
|---|---|---|---|
| | 3-2 | 3-3 | 3-4 |
| Zone 10 | 431.0 | 438.6 | 434.3 |
| Die Pressure (psi) | 998.7 | 758.37 | 769.05 |
| Pelletizer Speed (rpm | 1450 | 1450 | 1450 |
| Pelletizer Motor Load (%) | 15 | 15 | 15 |
| Water Temperature (° F.) | 120 | 120 | 120 |
| Pelletizer Water (GPM) | 50 | 50 | 50 |

The amount of work put into compounding the ethylene-hexene copolymers was less than 0.025 lbs/hr-hp.

Example 2

Blown Film from 100% of Resins 3-2, 3-3, and 3-4

Example 2A

Film (0.75 Mil, 60 Mil Die Gap, BUR 2.5:1)

While the manufacture of the blown film equipment is not limited, all example films containing 100 wt % of Resins 3-2, 3-3, and 3-4 were made into film using a 2.5 inch Gloucester blown film line equipped with a low work DSB-II screw, a 60 mil die gap and a Saturn Future Design Air Ring. The inventive resin was added to the hopper of the blow film line, and converted into blown films. The films were processed at a die throughput rate of 10 lbs/hr/die inch to produce a monolayer film having a thickness of 0.75 mil. The temperature of the melts was 400° F. More detailed film run conditions are reported in Table 5.

TABLE 5A

| | FILMS | | | |
|---|---|---|---|---|
| | Comparative | Inventive | | |
| | Resin | | | |
| | Exceed™ 1018 | 3-4 | 3-3 | 3-2 |
| $I_2$ (g/10 min.) | 1 | 1.2 | 1.1 | 0.44 |
| Density (g/cm$^3$) | 0.918 | 0.92 | 0.919 | 0.926 |
| Motor Load (%) | 68.2 | 44.8 | 44.8 | 56.7 |
| Torque (HP/RPM) | 0.361 | 0.237 | 0.237 | 0.300 |
| Extruder Head Pressure (psi) | 4020 | 2340 | 2340 | 3310 |
| Die Pressure (psi) | 2650 | 1490 | 1510 | 2220 |
| Specific Energy (Lbs/Hr-HP) | 8.74 | 13.08 | 13.23 | 9.94 |

Figure 5:
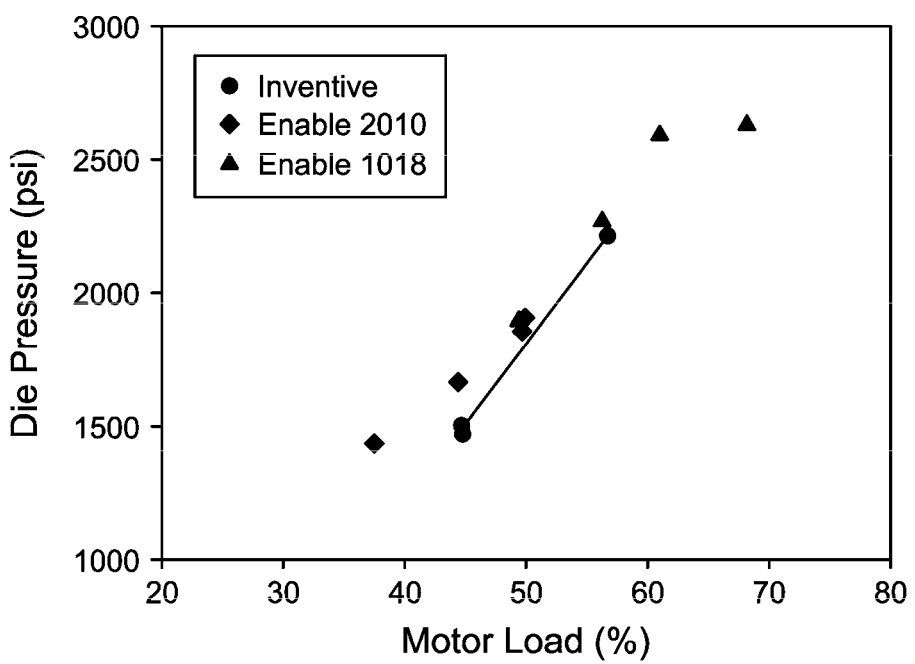
FIG. 5 shows the comparison of the processability of the inventive resin 3-2 to comparative commercial resins.

Total draw for the inventive films was observed to be twice that of the LDPE film, which typically have a maximum total draw of 40. The inventive films were easier to process than Exceed™ 1018 and Enable™ 20-10, thereby reducing motor load, torque and melt pressure (see FIG. 5). This leads to more efficient processability due to the decrease in frictional loss.

The films were tested and the film properties reported in Table 5B.

TABLE 5B

| | FILMS | | | | |
|---|---|---|---|---|---|
| | Comparative 1 | Inventive Resins | | | Comparative 2 |
| | Exceed™ 1018 | 3-4 | 3-3 | 3-2 | Enable™ 20-10 |
| $I_2$ (g/10 min.) | 1 | 1.2 | 1.1 | 0.44 | 1 |
| Density (g/cm³) | 0.918 | 0.92 | 0.919 | 0.926 | 0.92 |
| 1% Secant (psi) | | | | | |
| MD | 24,541 | 31,361 | 31,483 | 52,208 | 27,000 |
| TD | 27,238 | 42,971 | 43,711 | 75,652 | — |
| Elmendorf Tear | | | | | |
| MD (gms/mil) | 240 | 81 | 99 | 17 | 125 |
| TD (gms/mil) | 368 | 387 | 357 | 469 | 530 |
| Dart Impact, Phenolic, Method A | | | | | |
| (gms/mil) | 768 | 79 | ≤91 | <62.3 | 387 |
| Haze (%) | | | | | |
| Total | 24.2 | 14.5 | 19.8 | 25.6 | — |
| Internal | 1.1 | 1.2 | 1.2 | 1.1 | — |

The inventive resins 3-2, 3-3, and 3-4 offer superior stiffness when compared to Exceed™ 1018 and Enable™ 20-10 and similar or improved optical properties.

Example 2B

Film (0.75 Mil, 60 Mil Die Gap, BUR 4:1)

Increasing the blow up ratio to 4:1 appears to balance the film properties, as shown in the Table 6, below. Increasing the BUR from 2.5:1 to 4:1 changes the shrink performance, the TD/MD Elmendorf Tear ratio, the MD Elongation at break, and the dart drop (impact resistance).

TABLE 6

| | Resin | |
|---|---|---|
| | 3-2 | 3-2 |
| Gauge, mil (microns) | 0.75 (19) | 0.75 (19) |
| BUR | 2.5:1 | 4.0:1 |
| Die Gap | 60 | 60 |
| MD/TD Draw Ratio | 12.8 | 8 |
| 1% Secant Modulus MD (psi) | 52,208 | 42,312 |
| Ultimate Tensile Strength MD (psi) | 7,807 | 6,685 |
| Elongation @ Break MD (%) | 391 | 557 |
| Elongation @ Break TD (%) | 779 | 697 |
| Elmendorf Tear MD (g/mil) | 17 | 33 |
| Elmendorf Tear TD (g/mil) | 469 | 275 |
| TD/MD Ratio | 27.6 | 8.3 |
| Average (g/mil) | 243 | 154 |

TABLE 6-continued

| | Resin | |
|---|---|---|
| | 3-2 | 3-2 |
| Dart Drop (g/mil) | 62 | 120 |
| Shrink MD (%) | 81 | 74 |
| Shrink TD (%) | −6 | 21 |

Example 3

Physical Blends of Resins 3-2, 3-3, and 3-4

Example 3A 5 wt % Blends

Physical blends of 95 wt % Exceed™ 1018 and 5 wt % of inventive resin 3-2, 3-3, or 3-4 were extruded into films. Comparative blends comprising 95 wt % Exceed™ 1018 and 5 wt % of LDPE (LD 051 and LD 071) were also extruded into films.

Total Draw of 40, 0.75 Mil, 30 Mil Die Gap

Resin blends of Table 7 were made into film using a 2.5 inch blown film line equipped with a low work DSB-II screw, a 30 mil die gap and a Saturn Future Design Air Ring. The resin blend was added to the hopper of the blow film line, and converted into blown films. The films were processed at a die throughput rate of 10 lbs/hr/die inch to produce a monolayer film having a thickness of 0.75 mil. The temperature of the melt was 400° F. The film processing parameters and the film properties are reported in Table 7, below.

TABLE 7

| | 0.75 mil Films | | | | | | | |
|---|---|---|---|---|---|---|---|---|
| UNITS | Air Flow (%) | Frost Line Height (inches) | MD 1% Secant (psi) | MD Elmendorf Tear (gms/mil) | Dart Impact, Method A (gms/mil) | Haze (%) | Haze Internal (%) | Gloss 45° |
| 100 wt % Exceed ™ 1018 | 54 | 28 | 25698 | 228 | 535 | 16 | 1.1 | 36 |
| 5 wt % LD 051 | 71 | 23 | 31693 | 124 | 449 | 2 | 0.5 | 83 |
| 5 wt % LD 071 | 61 | 28 | 30427 | 145 | 500 | 2 | 0.6 | 83 |
| 5 wt % Resin 3-2 | 54 | 28 | 28246 | 213 | 461 | 4 | 0.8 | 73 |
| 5 wt % 3-3 | 59 | 31 | 27265 | 228 | 339 | 8 | 1.0 | 59 |
| 5 wt % Resin 3-4 | 59 | 30 | 27876 | 239 | 453 | 8 | 1.0 | 62 |

Total Draw of 10, 3 Mil, 30 Mil Die Gap

Resin blends were made into film using a 2.5 inch blown film line equipped with a low work DSB-II screw, a 30 mil die gap and a Saturn Future Design Air Ring. The resin blend was added to the hopper of the blow film line, and converted into blown films. The films were processed at a die throughput rate of 10 lbs/hr/die inch to produce a monolayer film having a thickness of 3 mil. The temperature of the melt was 410° F.

Performance of films made with blends of 95 wt % Exceed™ 1018 and 5 wt % of the inventive resins 3-2, 3-3, and 3-4 were evaluated and reported in Table 8, below. The inventive films demonstrated similar to superior stiffness when compared to 100 wt % Exceed™ 1018 and 5 wt % LDPE (LD 051 and LD 071) films. The inventive films also demonstrated a tear resistance similar to 100 wt % Exceed™ 1018 and superior to the 5 wt % LDPE films. The inventive films exhibited an impact resistance that was similar to that of the films made with 5% LDPE and a clarity that was superior to that of 100 wt % Exceed™ 1018 films, as shown in Table 8, below.

The inventive films demonstrated similar to superior stiffness when compared to Exceed™ 1018 and LDPE (LD 051 and LD 071). The inventive films also demonstrated a tear resistance superior to the LDPE films. The inventive films exhibited an impact resistance that was similar to that of the films made with LDPE and a clarity that was superior to that of Exceed™ 1018 films.

Figure 6A:
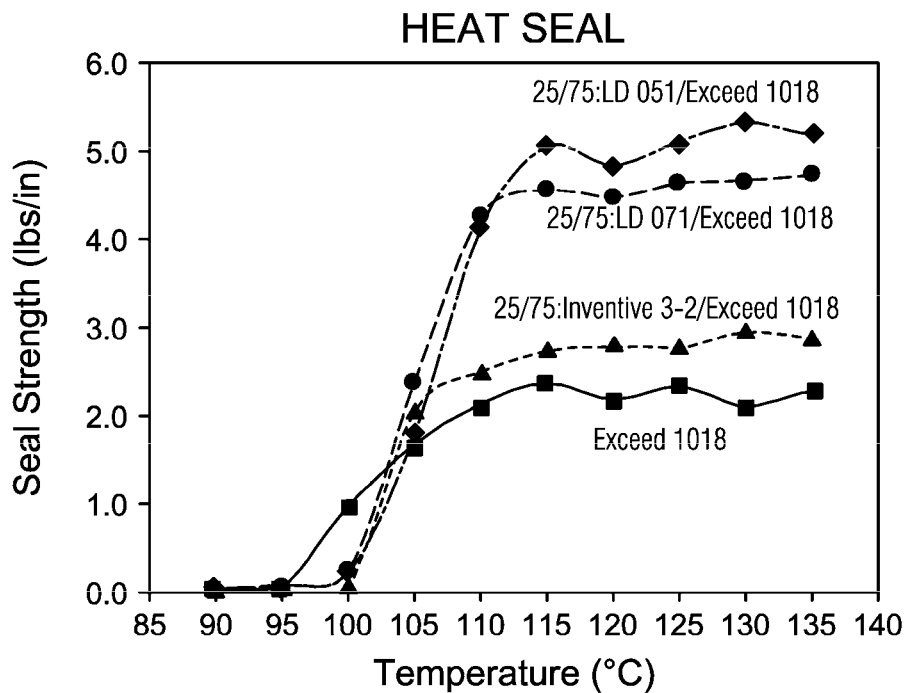
FIG. 6A shows the comparison of the heat seal performance of blends of the inventive resin 3-2 to comparative blends of commercial resins.
Figure 6B:
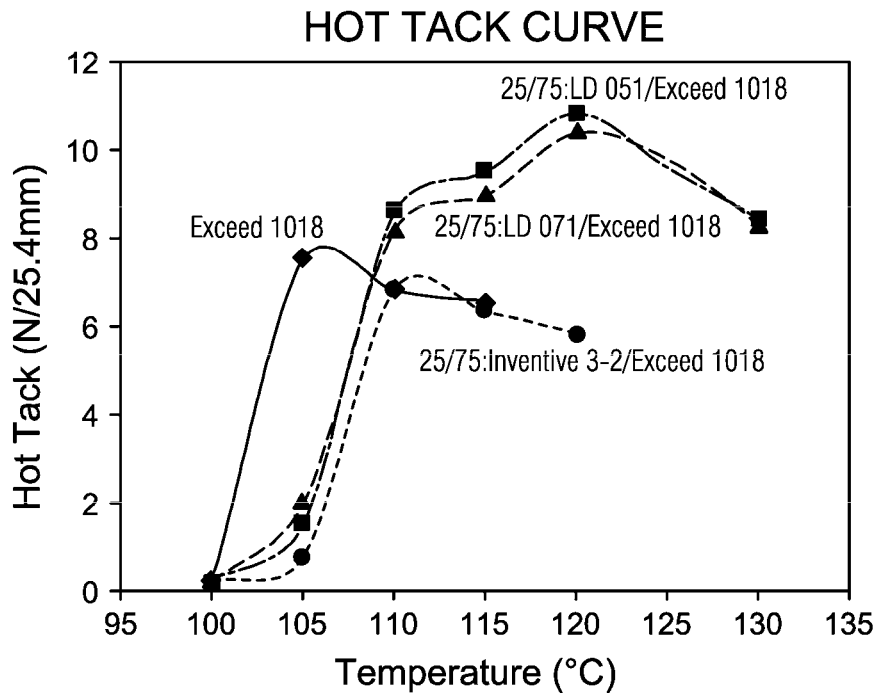
FIG. 6B shows the comparison of the hot tack performance of blends of the inventive resin 3-2 to comparative blends of commercial resins.

At 25 wt % loading, the film with resin 3-2 exhibited improved heat seal performance and similar hot tack performance when compared with films made from 100 wt % Exceed™ 1018 (see FIGS. 6A and 6B).

TABLE 8

| | 3 mil Films | | | | | | | |
| --- | --- | --- | --- | --- | --- | --- | --- | --- |
| Units | Air Flow (%) | Frost Line Height (inches) | MD 1% Secant (psi) | MD Elmendorf Tear (gms/mil) | Dart Drop, Method A (gms/mil) | Haze (%) | Haze Internal (%) | Gloss 45° — |
| 100 wt % Exceed ™ 1018 | 56.2 | 29 | 29075 | 296 | 450 | 31 | 16 | 32 |
| 5 wt % LD 051 | 65.7 | 27 | 29434 | 267 | 444 | 5 | 3 | 79 |
| 5 wt % LD 071 | 60 | 28 | 30084 | 283 | 442 | 6 | 4 | 78 |
| 5 wt % Resin 3-2 | 51.9 | 33 | 30581 | 289 | 450 | 14 | 7 | 55 |
| 5 wt % Resin 3-3 | 56.2 | 31 | 29996 | 292 | 451 | 25 | 13 | 36 |
| 5 wt % Resin 3-4 | 58.5 | 30 | 30115 | 297 | 451 | 24 | 11 | 39 |

Example 3B

Films Made from 25% Blends

Physical blends of 75 wt % Exceed™ 1018 and 25 wt % of inventive resin 3-2, 3-3, or 3-4 were compounded. Comparative blends of 75 wt % Exceed™ 1018 and 25 wt % of LDPE (LD 051 and LD 071) were also compounded.

Total Draw of 60, 1 Mil, 60 Mil Die Gap

Resin blends were made into film using a 2.5 inch blown film line equipped with a low work DSB-II screw, a 60 mil die gap and a Saturn Future Design Air Ring. The resin blend was added to the hopper of the blow film line, and converted into blown films. The films were processed at a die throughput rate of 10 lbs/hr/die inch to produce a monolayer film having a thickness of 1 mil. The temperature of the melt was 400° F.

Performance of films made with blends of 75 wt % Exceed™ 1018 and 25 wt % of the inventive resins 3-2, 3-3, and 3-4 were evaluated and reported in Table 9A, below.

Total Draw of 10, 3 Mil, 30 Mil Die Gap

Resin blends were made into film using a 2.5 inch blown film line equipped with a low work DSB-II screw, a 30 mil die gap and a Saturn Future Design Air Ring. The resin blend was added to the hopper of the blow film line, and converted into blown films. The films were processed at a die throughput rate of 10 lbs/hr/die inch to produce a monolayer film having a thickness of 3.0 mil. The temperature of the melt was 410° F.

Performance of films made with blends of 75 wt % Exceed™ 1018 and 25 wt % of the inventive resins 3-2, 3-3, and 3-4 were evaluated and reported in Table 9B, below.

TABLE 9A

| | Film (1 mil, 60 mil die gap) | | | | | |
| --- | --- | --- | --- | --- | --- | --- |
| Units | MD 1% Secant (psi) | MD Elmendorf Tear (gms/mil) | Dart Drop, Method A (gms/mil) | Haze (%) | Haze Internal (%) | Gloss 45° — |
| 100 wt % Exceed ™ 1018 | 24615 | 244 | 707 | 41 | 1.7 | 23 |
| 25 wt % LD 051 | 38232 | 24 | 191 | 8 | 0.8 | 60 |
| 25 wt % LD 071 | 39265 | 30 | 169 | 3 | 0.6 | 83 |
| 25 wt % Resin 3-2 | 32022 | 99 | 247 | 6 | 1.0 | 66 |

TABLE 9B

| | Film (3 mil, 30 mil die gap) | | | | | |
|---|---|---|---|---|---|---|
| | 100 wt % Exceed ™ 1018 | 25 wt % LD 051 | 25 wt % LD 071 | 25 wt % 3-2 | 25 wt % 3-3 | 25 wt % 3-4 |
| Motor load (%) | 69.1 | 65 | 62.4 | 67.4 | 64.7 | 63.6 |
| Torque (HP/rpm) | 0.366 | 0.344 | 0.33 | 0.357 | 0.343 | 0.337 |
| Die pressure (psi) | 3490 | 3570 | 3440 | 3450 | 3260 | 3230 |
| Air Flow (%) | 56.2 | 65.7 | 60 | 51.9 | 56.2 | 58.5 |
| Frost Line Height (inches) | 29 | 14 | 20 | 28 | 29 | 27 |
| MD 1% Secant (psi) | 29,075 | 27,323 | 29,728 | 33,709 | 30,407 | 30,331 |
| MD Elmendorf Tear (g/mil) | 296 | 106 | 148 | 283 | 288 | 299 |
| Dart Drop (g/mil) | 450 | 200 | 217 | 357 | 363 | 345 |
| Haze (%) | 31 | 8 | 5 | 13 | 21 | 18 |
| Haze Internal (%) | 15.6 | 2.1 | 2.7 | 6.6 | 11.5 | 9.4 |
| Gloss 45° | 32 | 64 | 81 | 60 | 47 | 54 |

The blends had desirable processability similar to LDPE blends. The inventive films also demonstrated superior bubble stability, superior MD tear resistance, and superior impact resistance when compared to LDPE blends.

Example 4

Films Made from 5 Wt % to 75 Wt % Blends

Physical blends of from 95 wt % to 25 wt % Exceed™ 1018 and from 5 wt % to 75 wt % of inventive resin 3-2, 3-3, or 3-4 were compounded. Comparative blends of 95 wt % to 25 wt % Exceed™ 1018 and from 5 wt % to 75 wt % of LDPE (LD 051 and LD 071) were also compounded.

Film process conditions were fixed at a total draw of 10, 3 mil film, 30 mil die gap, 410° F. 2.5:1 BUR, and 10 lbs/hr/die inch. Under these conditions, film made from neat Exceed™ 1018 was unstable and hard to produce. Indeed, the film had an observed melt temperature of 411° F.

Comparative films made with greater than 25 wt % LDPE could not be processed into film, for example, the maximum draw for LD 051 blend was 10. Additionally, films with 60 wt % and 75 wt % LD 071 required the maximum airflow the line could deliver and were marginally stable, indicating that these formulations were at the limit of the line's processing capabilities.

Figure 7A:
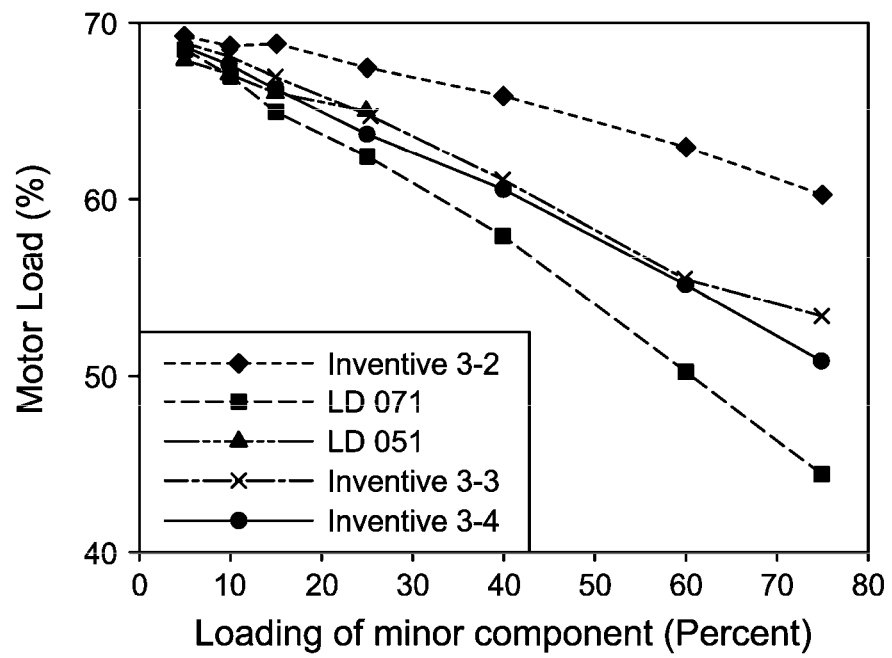
FIG. 7A shows the comparison of the extruder motor load of blends of the inventive resins 3-2, 3-3, and 3-4 to comparative blends of commercial resins.
Figure 7B:
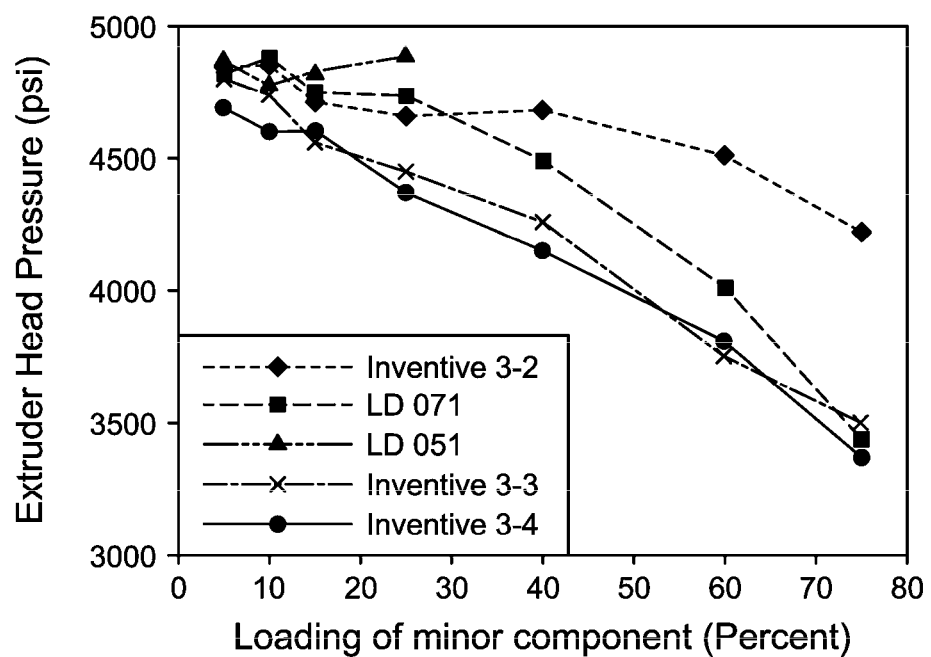
FIG. 7B shows the comparison of the extruder head pressure of blends of the inventive resins 3-2, 3-3, and 3-4 to comparative blends of commercial resins.
Figure 7C:
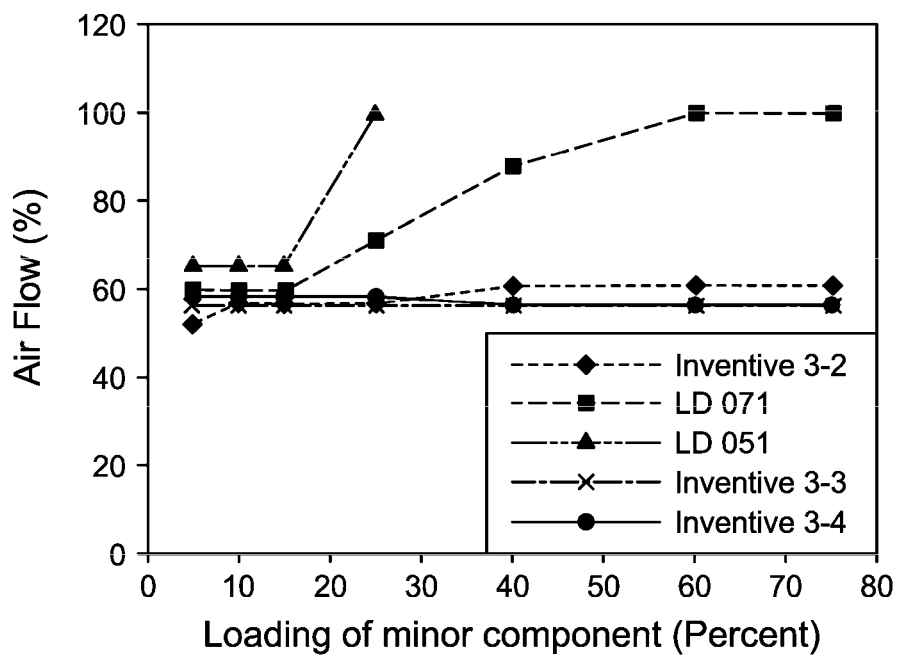
FIG. 7C shows the comparison of the air flow of blends of the inventive resins 3-2, 3-3, and 3-4 to comparative blends of commercial resins.
Figure 7D:
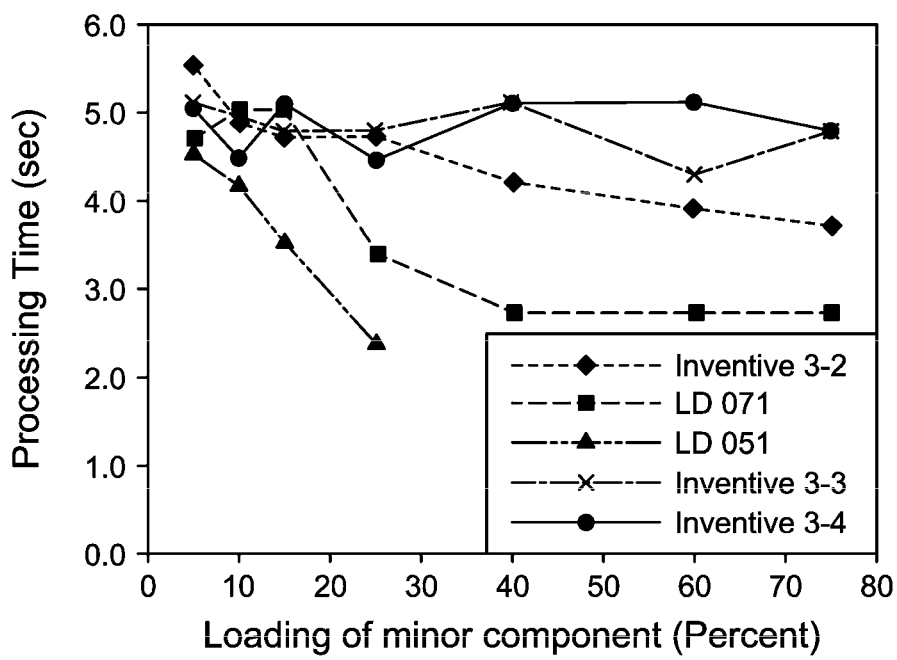
FIG. 7D shows the comparison of the processing time of blends of the inventive resins 3-2, 3-3, and 3-4 to comparative blends of commercial resins.
Figure 8A:
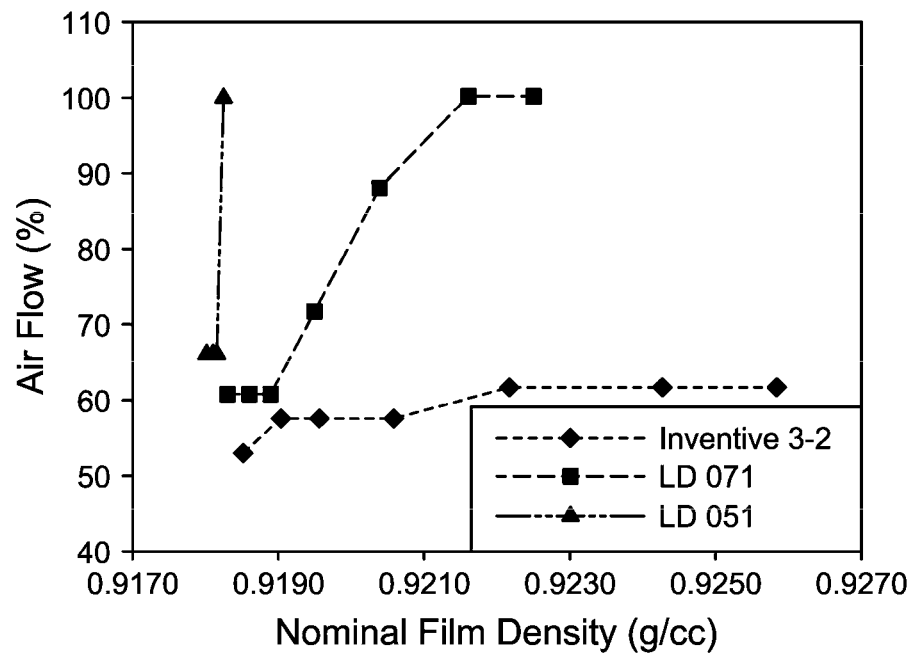
FIG. 8A shows the comparison of the air flow of blends of the inventive resins 3-2, 3-3, and 3-4 to comparative blends of commercial resins, as a function of nominal film density.
Figure 8B:
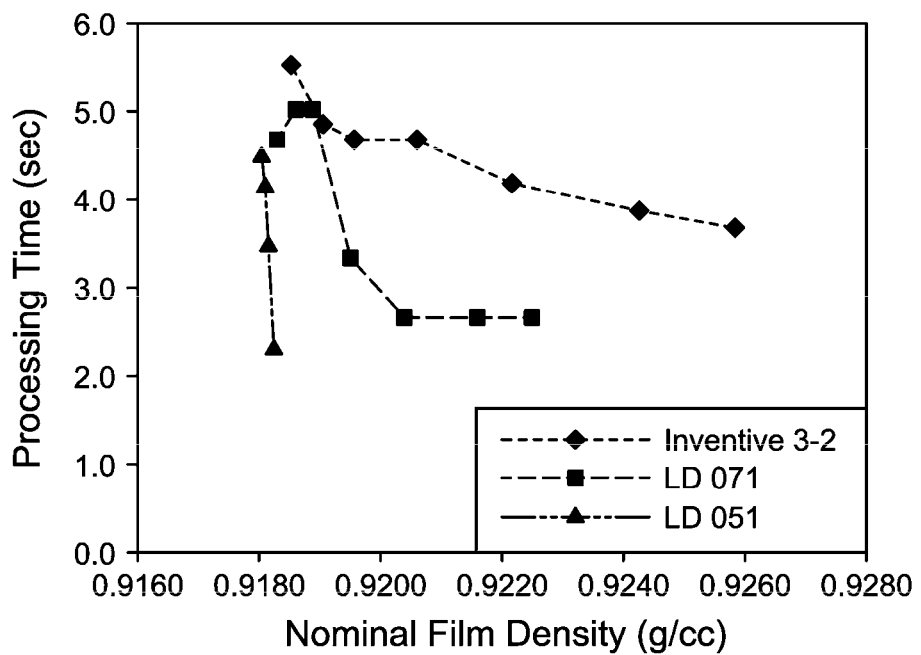
FIG. 8B shows the comparison of the processing time of blends of the inventive resins 3-2, 3-3, and 3-4 to comparative blends of commercial resins, as a function of nominal film density.

In contrast, films were easily made with blends of 5 wt % to 75 wt % inventive resins 3-2, 3-3, and 3-4 and 95 wt % to 25 wt % Exceed™ 1018. All the blends with inventive resins were easily processed into film. Indeed, the blends with inventive resins had reduced extruder motor load, extruder pressures and die pressures (see FIGS. 7A and 7B). Additionally, the films made from blends with inventive resins were more stable, that is had better bubble stability than the comparative films. The films made from blends with inventive resins required lower air flow rates (see FIGS. 7C and 8A), requiring less air to keep the bubble in the pocket and better processing time (see FIGS. 7D and 8B) than the comparative films. Indeed at a 25 wt % loading, the inventive films prove easier to process over a broader density range (see FIG. 8A) and have more consistent processing time over a broader density range (see FIG. 8B). This combination of useful properties effectively expands the film manufacturing window, when compared to traditional LDPEs.

Figure 9A:
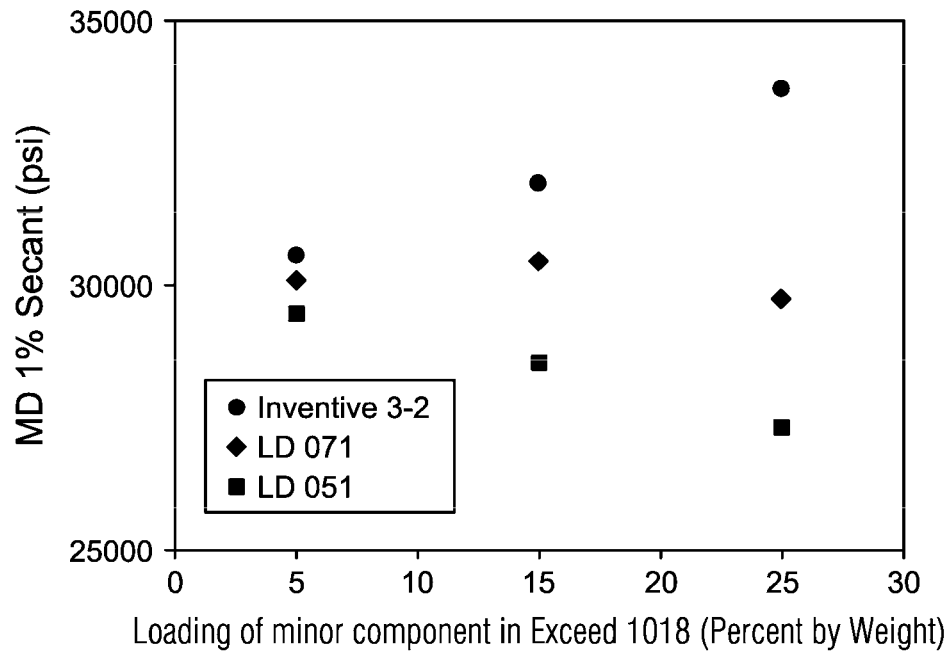
FIG. 9A shows the comparison of the film stiffness of films of blends of the inventive resin 3-2 to films of comparative blends of commercial resins, as a function of loading of the minor component.
Figure 9B:
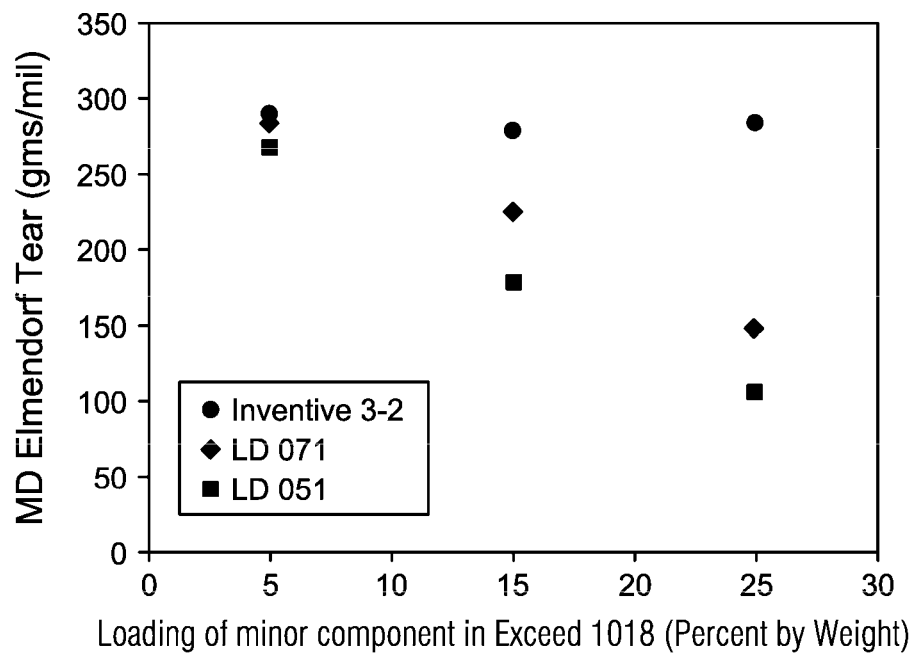
FIG. 9B shows the comparison of the MD Elmendorf Tear of films of blends of the inventive resin 3-2 to films of comparative blends of commercial resins, as a function of loading of the minor component.

The film properties were assessed. Film stiffness increased with increasing inventive resin 3-2 content. In contrast, film stiffness decreased with increasing comparative LDPE content (see FIG. 9A). Film tear resistance was fairly constant despite increasing inventive resin content. In contrast, the film tear resistance decreased with increasing LDPE content (see FIG. 9B).

Figure 10A:
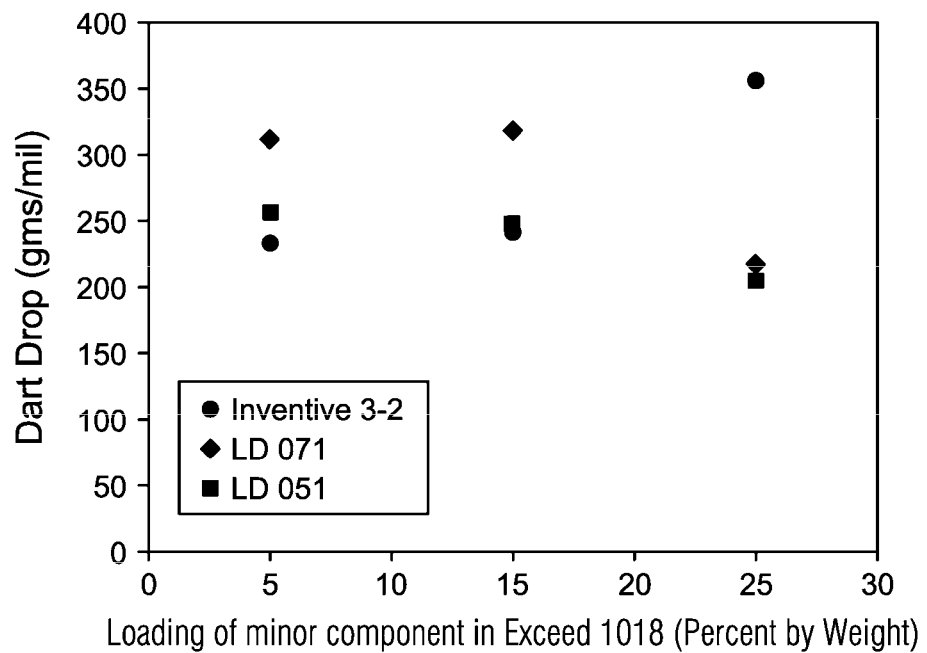
FIG. 10A shows the comparison of the Dart Drop of films of blends of the inventive resin 3-2 to films of comparative blends of commercial resins, as a function of loading of the minor component.
Figure 10B:
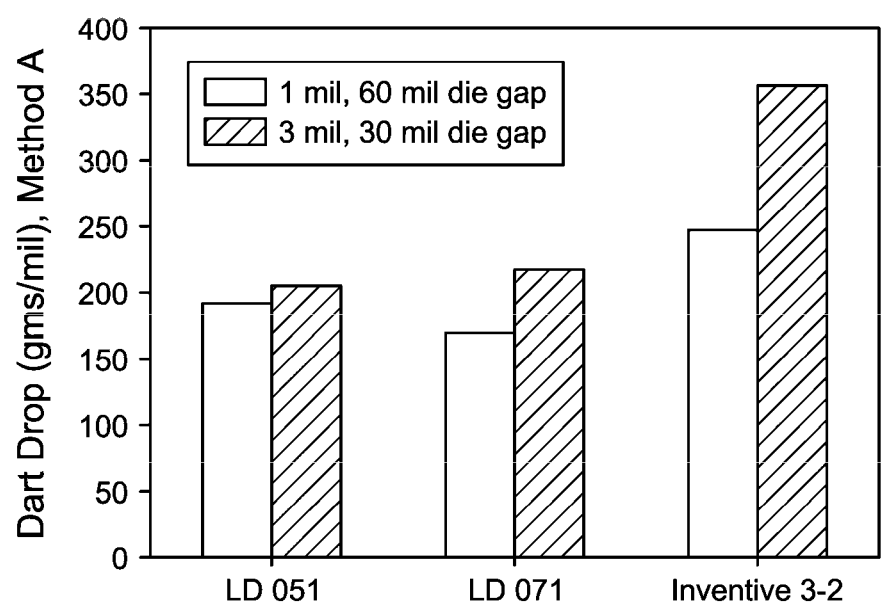
FIG. 10B shows the comparison of the Dart Drop of films of blends of the inventive resin 3-2 to films of comparative blends of commercial resins, as a function of film thickness.
Figure 11:
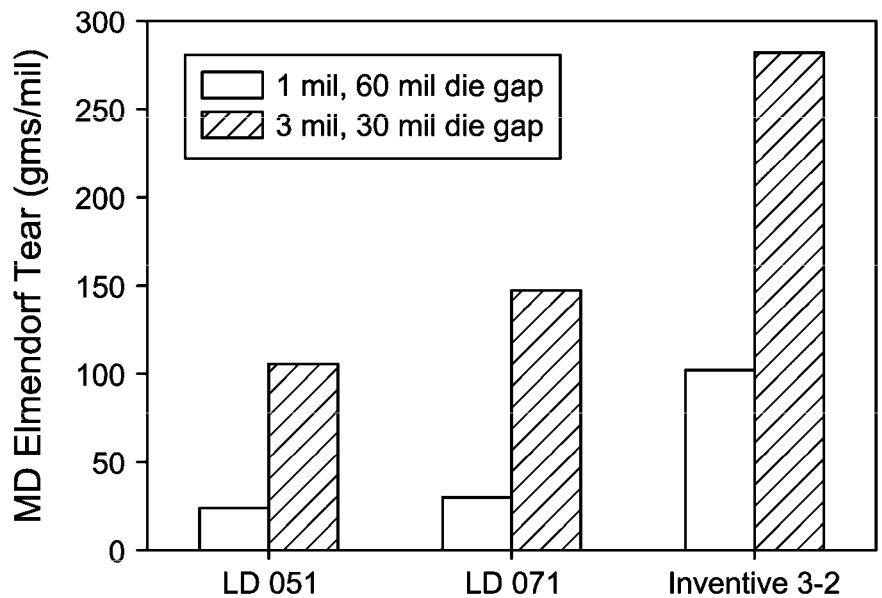
FIG. 11 shows the comparison of the MD Elmendorf Tear of films of blends of the inventive resin 3-2 to films of comparative blends of commercial resins, as a function of die gap and film gauge (thickness).

Additionally, at a 25 wt % loading, the film with resin 3-2 exhibited improved impact resistance (by more than 50%), compared with a decreased impact resistance at a 25 wt % loading of LDPE (see FIGS. 10A and 10B). This improved impact resistance was observed to be consistent over various film thicknesses (see FIG. 10B).

Similarly, at a 25 wt % loading, the film with resin 3-2 exhibited increased MD tear resistance by more than 50% (see FIG. 10E).

Example 5

In-Reactor Blends

Ethylene-hexene copolymer was made by reacting ethylene with hexene using a silica supported mixed catalyst, that is, 25 wt % dimethylsilylene(2,3,4,5-tetramethyl-1-cyclopentadienyl)(3-phenyl-1-indenyl)zirconium dichloride and 75 wt % bis(1-methyl,3-butylcyclopentadienyl)zirconium dichloride, supported on a single silica support (Mixed Catalyst A) and activated with MAO. Four yields were collected under slightly different polymerization conditions (resins 1, 2, 2-3, and 4).

Polymerization Methods

The polymerization was conducted in a laboratory gas phase reactor having a fluidized bed reactor equipped with devices for temperature control, catalyst feeding or injection equipment, gas chromatograph analyzer for monitoring and controlling monomer and gas feeds, and equipment for polymer sampling and collecting. The reactor consisted of a 6" (15.24 mm) diameter bed section increasing to 10" (25.4 mm) at the reactor top. Gas came in through a perforated distributor plate allowing fluidization of the bed contents and polymer sample was discharged at the reactor top. The reactor was operated as shown in Table 10, below.

TABLE 10

| | Resin | | | |
|---|---|---|---|---|
| | 1 | 2 | 2-3 | 4 |
| | Catalyst | | | |
| | Mixed Catalyst A | Mixed Catalyst A | Mixed Catalyst A | Mixed Catalyst A |
| Temperature, °F. (°C.) | 167 (75) | 176 (80) | 185 (85) | 210 (99) |
| Hexene (mol %) | 1.63 | 1.63 | 1.63 | 1.98 |
| Hydrogen (ppm) | 105 | 105 | 105 | 210 |
| Hydrogen/Ethylene Ratio (ppm/%) | 1.5 | 1.5 | 1.5 | 3.0 |
| $I_2$ (g/10 min.) | 0.9 | 0.6 | 0.6 | 0.6 |
| Density (g/cm$^3$) | 0.9201 | 0.9275 | 0.9342 | 0.9278 |

Productivity was 7,000 lbs resin/lb of catalyst and the production rate was 50 lbs of resin per hour.

The ethylene-hexene copolymers listed in Table 10 were stabilized with an additive package comprising 500 ppm Irganox 1076, 1000 ppm Irgafos 168, and 800 ppm Dynamar FX-5920A, and compounded.

Films Made with In-Reactor Blends 100 wt % in-reactor blend resins were made into film using a 2.5 inch blown film line equipped with a low work DSB-II screw, a 60 mil die gap and a Saturn Future Design Air Ring. The resin blend was added to the hopper of the blow film line, and converted into blown films. The films were processed at a die throughput rate of 10 lbs/hr/die inch to produce a monolayer film having a thickness of 0.75 mil. The temperature of the melt was 400° F. The films were compared with films made from 100% Exceed™ 1018.

The processability parameters (extruder motor load and extruder head pressure) are reported along with film properties in Table 11, below.

TABLE 11

| | Material | | | | |
|---|---|---|---|---|---|
| | Comparative | Inventive | | | |
| | | Resins | | | |
| | Exceed™ 1018 | 1 | 2 | 4 | 2/3 |
| Motor load (%) | 69 | 70 | 69 | 69 | 63 |
| Extruder Head Pressure (psi) | 4050 | 4150 | 4850 | 4920 | 4480 |
| $I_2$ (g/10 min.) | 1 | 0.9 | 0.6 | 0.6 | 0.6 |
| Density (g/cm$^3$) | 0.918 | 0.9201 | 0.9275 | 0.9278 | 0.9342 |
| | 1% Secant (psi) | | | | |
| MD | 23861 | 27456 | 46610 | 46033 | 61658 |
| | Elmendorf Tear | | | | |
| MD (g/mil) | 213 | 253 | 49 | 66 | 33 |
| TD (g/mil) | 424 | 556 | 988 | 835 | 275 |
| | Dart Drop, Phenolic, Method A | | | | |
| (g/mil) | 732 | 302 | 140 | 145 | 64 |

Example 6

Additional Polymer and Film Characterization

In Tables 12 and 13 below include further characterization data for the inventive ethylene-based copolymers. Films of 0.75 mil (19 μm) were made as described above, and characterized for their processability as shown in Table 14, and the film characterized in Table 15. Also, in-reactor blends were also demonstrated as shown in Tables 14 and 15, where two metallocene catalysts were on one support and used in a gas phase polymerization process. The branching factor (g' value in Table 12) indicates the presence of long chain branched material in the resin, which for the inventive ethylene-based polymers is located in the higher molecular weight fractions of the resin.

TABLE 12

| | Molecular Structure | | | |
|---|---|---|---|---|
| | Exceed | Inventive | | |
| | 1018 | 3-4 | 3-3 | 3-2 |
| $I_2$ (g/10 min) | 1.0 | 1.31 | 1.11 | 0.49 |
| MIR ($I_{22}/I_2$) | 20 | 37 | 40 | 40 |
| Density (g/cm$^3$) | 0.9180 | 0.9209 | 0.9204 | 0.9285 |

TABLE 12-continued

| | Molecular Structure | | | |
|---|---|---|---|---|
| | Exceed | Inventive | | |
| | 1018 | 3-4 | 3-3 | 3-2 |
| | MALLS/3D GPC Results | | | |
| Mw | 10,9001 | 14,9555 | 15,2714 | 17,4637 |
| Mw/Mn | 2.9 | 4.1 | 4.0 | 4.1 |
| Mz/Mw | 2.3 | 3.7 | 3.6 | 3.4 |
| Mz/Mn | 6.6 | 15.2 | 14.4 | 13.8 |
| g' (Vis. Ave.) | 0.84 | 0.706 | 0.688 | 0.723 |
| g' (Z. Ave.) | >0.8 | 0.546 | 0.529 | 0.571 |
| g' (Ultimate) | >0.8 | <0.5 | <0.5 | <0.5 |

The inventive ethylene-based copolymers most preferably have a density of at least 0.920 g/cm$^3$, an MIR of greater than 35, a g'(vis·ave) of less than 0.80, and an Mz/Mn of greater than 8.

TABLE 13

| | Unsaturation Content | | | |
|---|---|---|---|---|
| On a per K | Inventive | | | |
| carbon basis: | 3-2 | 3-3 | 3-4 | Exceed 1018 |
| Vinyls | 0.27 | 0.29 | 0.35 | 0.03 |
| Vinylenes | 0.09 | 0.08 | 0.14 | 0.06 |

TABLE 13-continued

| | Unsaturation Content | | | |
|---|---|---|---|---|
| On a per K | Inventive | | | |
| carbon basis: | 3-2 | 3-3 | 3-4 | Exceed 1018 |
| Vinylidenes | 0.08 | 0.08 | 0.10 | 0.03 |
| trisubstituted | 0.13 | 0.06 | 0.12 | 0.10 |

The inventive ethylene-based copolymers most preferably have has within the range from 0.10 or 0.15 to 0.40 or 0.50 terminal vinyl groups per 1000 carbons. The processability assessment of the polymer and blends shows a reduced motor load and head pressure.

TABLE 14

| | Resin Characterization and Film Processability | | | | | | | | |
|---|---|---|---|---|---|---|---|---|---|
| | | Inventive | | | | 75 wt % LLDPE*/25 wt % Inventive PE *Exceed 1018 | | | |
| parameter | Exceed 1018 | 3-4 | 3-3 | 3-2 | 3-2 | 1 | 2 | 3 | 4 |
| I$_2$ (g/10 min, 190° C.) | 1.0 | 1.31 | 1.11 | 0.49 | 0.49 | 0.87 | 0.59 | 0.57 | 0.58 |
| I$_{21}$ (g/10 min, 190° C.) | 20 | 48.2 | 44.1 | 19.5 | 19.5 | 14 | 10 | 9 | 11 |
| I$_{22}$/I$_2$ | 20 | 36.7 | 39.6 | 39.7 | 39.7 | 16 | 17 | 16 | 19 |
| Density (g/cm$^3$) | 0.918 | 0.9209 | 0.9204 | 0.9285 | 0.9285 | 0.9201 | 0.9275 | 0.9278 | 0.9342 |
| Die Gap | 60 | 60 | 60 | 60 | 60 | 60 | 60 | 60 | 60 |
| BUR | 2.5:1 | 2.5:1 | 2.5:1 | 2.5:1 | 4:1 | 2.5 | 2.5 | 2.5 | 2.5 |
| Production Rate (lbs/hr) | 189 | 187 | 189 | 187 | 188 | 187 | 189 | 188 | 186 |
| Melt Temp, ° F. (° C.) | 405 (207) | 393 (200) | 393 (200) | 399 (204) | 399 (204) | 405 (207) | 409 (209) | 409 (209) | 410 (210) |
| Specific Output (lbs/rpm) | 3.15 | 3.1 | 3.13 | 2.98 | 2.91 | 3.1 | 2.83 | 2.79 | 2.36 |
| Motor Load (%) | 68.2 | 44.8 | 44.8 | 56.7 | 57.7 | 70 | 69 | 69 | 63 |
| Extruder Head Pressure (psi) | 4020 | 2340 | 2340 | 3310 | 3380 | 4150 | 4850 | 4920 | 4480 |
| Air Flow Rate (%) | 67.4 | 67.4 | 67 | 84.3 | 60 | 70.8 | 86.7 | 86.7 | 86.7 |
| Processing Time (sec) | 1.9 | 1.5 | 1.4 | 1.2 | 4.2 | 1.6 | 1.2 | 1.2 | 1.2 |

TABLE 15

| | Film Characterization | | | | | | | |
|---|---|---|---|---|---|---|---|---|
| | Exceed | Inventive | | | 75 wt % LLDPE*/25 wt % Inventive PE *Exceed 1018 | | | |
| Parameter | 1018 | 3-4 | 3-3 | 3-2 | 1 | 2 | 3 | 4 |
| MD 1% Secant Modulus (psi) | 24,541 | 31,361 | 31,483 | 52,208 | 27,456 | 46,610 | 46,033 | 61,658 |
| MD Ultimate Tensile Strength (psi) | 11,878 | 6042 | 5957 | 7807 | 7429 | 10,659 | 10,664 | 10,985 |
| MD Elongation at Break (%) | 507 | 440 | 408 | 391 | 387 | 388 | 403 | 441 |
| TD Elongation at Break (%) | 655 | 759 | 729 | 779 | 650 | 726 | 720 | 804 |
| Elmendorf Tear, MD (g/mil) | 240 | 81 | 99 | 17 | 253 | 49 | 66 | 33 |
| Elmendorf Tear, TD (g/mil) | 368 | 387 | 357 | 469 | 556 | 988 | 835 | 275 |

TABLE 15-continued

Film Characterization

| Parameter | Exceed 1018 | Inventive 3-4 | Inventive 3-3 | Inventive 3-2 | 75 wt % LLDPE*/25 wt % Inventive PE *Exceed 1018 | | | |
|---|---|---|---|---|---|---|---|---|
| | | | | | 1 | 2 | 3 | 4 |
| TD/MD | 1.5 | 4.8 | 3.6 | 27.6 | 2.2 | 20.2 | 12.7 | 8.3 |
| Average (g/mil) | 304 | 234 | 228 | 243 | 405 | 519 | 451 | 154 |
| Dart Drop (g/mil) | 768 | 79 | 91 | 62 | 302 | 140 | 145 | 64 |

Air flow rate measure of a resin's melt strength during extrusion. Melts with increased elongational viscosity require greater air flow to be held in the pocket during extrusion. Lower density ethylene-based copolymer containing films will give improved tear resistance: MD tear resistance decreases with increasing resin density, MD tear resistance is greater for $1.0-I_2$ resins, and MD tear resistance decreases with an increase in the resin $I_{22}$, with $1.0-I_2$ resins being more responsive than fractional $I_2$ resins. Lower density ethylene-based copolymer containing films will improved impact resistance: impact resistance decreases with increasing resin density, impact resistance may increase with increasing $I_{22}$ for in-reactor blends, and impact resistance is independent of $I_{22}$ for resins made using ethylene-based copolymer alone. The impact resistance surprisingly increases with increasing MD tear resistance for in-reactor blends.

Example 7

Demonstrated Benefits of Film

Long chain branched resins provides converters with the advantage of improved extrudability, that is, higher production rates, without modifying their equipment. For example, the motor load for high pressure low density resins (high pressure-LDPE resins like LD140 and LD 113) is about 35% of that of metallocene catalyzed liner low density resins (m-LLDPE resins like Exceed 1018 resin), while extruder and die pressures are about half those observed for the m-LLDPE resin. Hence, the high pressure-LDPE resins offer blown film converters the opportunity to expand the production capabilities of their existing film lines by at least 50%, a distinct commercial advantage, as shown in Table 16.

TABLE 16

Processability of commercial polyethylenes
Extrusion Performance of Selected HP-LDPE resins

| | Resins | | |
|---|---|---|---|
| | Exceed | HP-LDPE | |
| Property | 1018CA | 140.09 | 113.09 |
| MI-2 (g/10 min) | 1 | 0.75 | 2.25 |
| Density (g/cc) | 0.918 | 0.921 | 0.919 |
| Melt Temp (° F.) | 400 | 361 | 350 |
| Extrusion Rate (lb/hr) | 188 | 181 | 182 |
| Motor Load (%) | 68.2 | 36 | 30 |
| Torque (Hp/RPM) | 0.4 | 0.2 | 0.2 |
| Extruder Head Pressure (psi) | 4020 | 2520 | 1750 |
| Die Pressure (psi) | 2650 | 2000 | 1460 |

Long chain branched resins provides converters with the advantage of improved melt strength that results in better bubble stability, bigger bubbles and thicker films, 6 mil films using blow up ratio of 4:1. For example, the melt strength of LD-071 and LD-051 resins (both high-pressure LDPEs) are an order of magnitude greater than that of Exceed 1018 resin, as shown in Table 17, where Drawability=Die gap/film gauge, and "extensibility" is related to the melt strength of the resins or blend.

TABLE 17

Drawability
Selected Resins

| | | Resin | | |
|---|---|---|---|---|
| | | HP-LDPE | | Exceed |
| Property | Units | 051 | 071 | 1018 |
| Melt Index | (g/10 min) | 0.25 | 0.75 | 1.0 |
| Density | (g/cc) | 0.919 | 0.921 | 0.918 |
| Melt Strength | (cN) | 23 | 11 | 1.4 |
| Extensibility | — | 9 | 20 | 31 |
| Drawability | | 30 | 40 | 80 |

HP-LDPE resins have reduced drawability compared to m-LLDPE resins. The drawability of m-LLDPE resins exceeds 80, while that of LD-071 and LD-051 are less than 50.

Commercial blown film operations typical use die gaps ranging between 30 mil and 120 mil, with most commercial blown film operations using die gaps of 45 mil or more, and preferable 60 mil or more. However, selected shrink film applications require using 30 mil die gaps to achieve optimum film performance, specifically, shrink performance. Converters prefer to use wider die gaps since wider die gaps increase their production capacity. For example, wider die gaps are used in making cost competitive films such as trash can liners, which are thin (0.75 mil) films. Hence, HP-LDPE resins limit the films that can be made from any blown film line.

Figure 12:
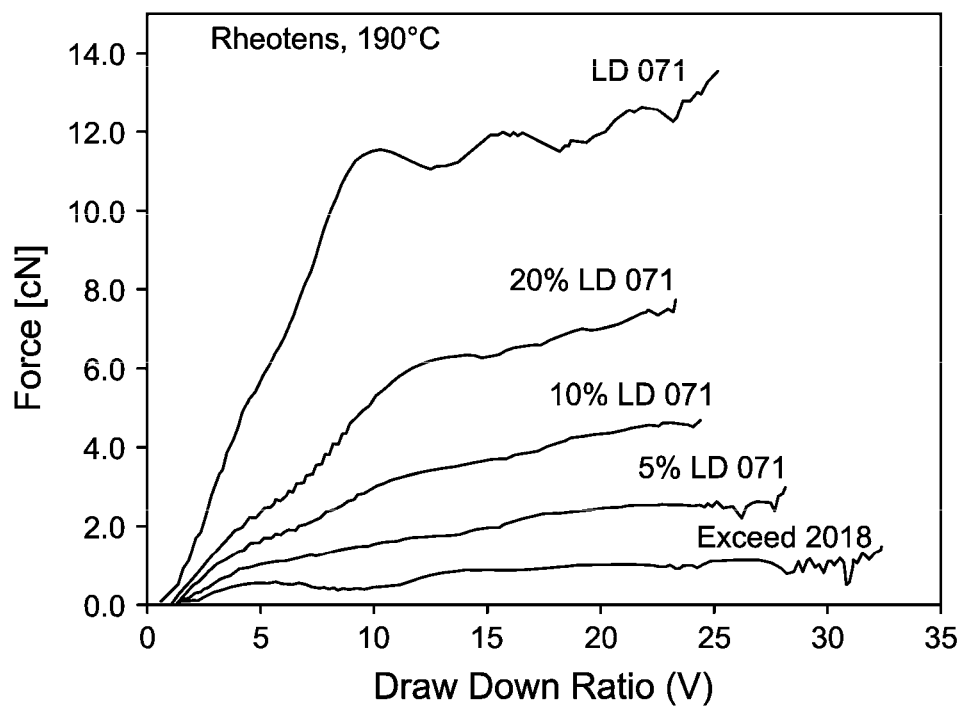
FIG. 12 shows a comparison of Melt Strength of various polyethylene resins and blends as a function of Melt Strength.

HP-LDPE resins improve productivity of m-LLDPE resins by reducing the motor load and improving melt strength, but reduce the film's toughness balance: impact-MD tear resistance, as shown in Table 18 and FIG. 12.

TABLE 18

Melt Strength and Extensibility

| | Blend Composition (in LDPE-071) | | | | |
|---|---|---|---|---|---|
| | 0 wt % | | | | |
| Property | Exceed 1018 | 5 wt % | 10 wt % | 15 wt % | 100 wt % |
| $I_2$ (g/min) (190° C.) | 2.0 | 1.7 | 1.4 | 1.2 | 0.75 |
| Density (g/cm3) | 0.918 | 0.9181 | 0.9182 | 0.9183 | 0.92 |
| Melt Strength (cN) | 1.4 | 2.5 | 4.5 | 7.5 | 11 |
| Extensibility | 31 | 25 | 22 | 22 | 20 |

Figure 13:
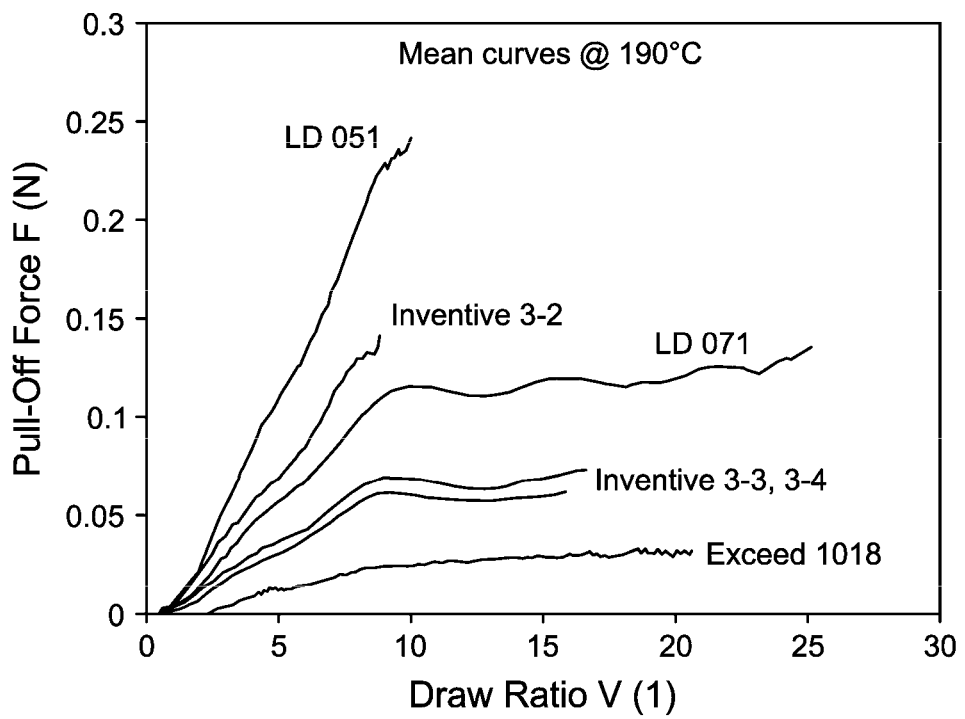
FIG. 13 shows a comparison of Pull-Off Force of various polyethylene resins and inventive resins as a function of Draw Ratio.

The inventive long chain branched metallocene catalyzed liner low density resins (ethylene-based copolymers) have improve productivity compared to m-LLDPE resins due to reduced motor load and improving melt strength, as shown in Table 19 and FIG. 13.

TABLE 19

| | Processability of Inventive ethylene-based copolymers | | | |
|---|---|---|---|---|
| | | | Inventive | |
| Property | Exceed 1018 | 3-4 | 3-3 | 3-2 |
| $I_2$ (g/10 min) (190° C.) | 1.0 | 1.31 | 1.11 | 0.49 |
| Density (g/cm$^3$) | 0.918 | 0.9209 | 0.9204 | 0.9285 |
| MD 1% Secant Modulus (psi) | 24,541 | 31,361 | 31,483 | 52,208 |
| Dart Impact (Method A) (g/mil) | 768 | 79 | 91 | 62 |
| MD Elmendorf Tear (g/mil) | 240 | 81 | 99 | 17 |
| Motor Load (%) | 68.2 | 44.8 | 44.8 | 56.7 |
| Torque (HP/rpm) | 0.4 | 0.2 | 0.2 | 0.3 |
| Extruder Head Pressure (psi) | 4020 | 2340 | 2340 | 3310 |
| Die Pressure (psi) | 2650 | 1490 | 1510 | 2220 |

Figure 14:
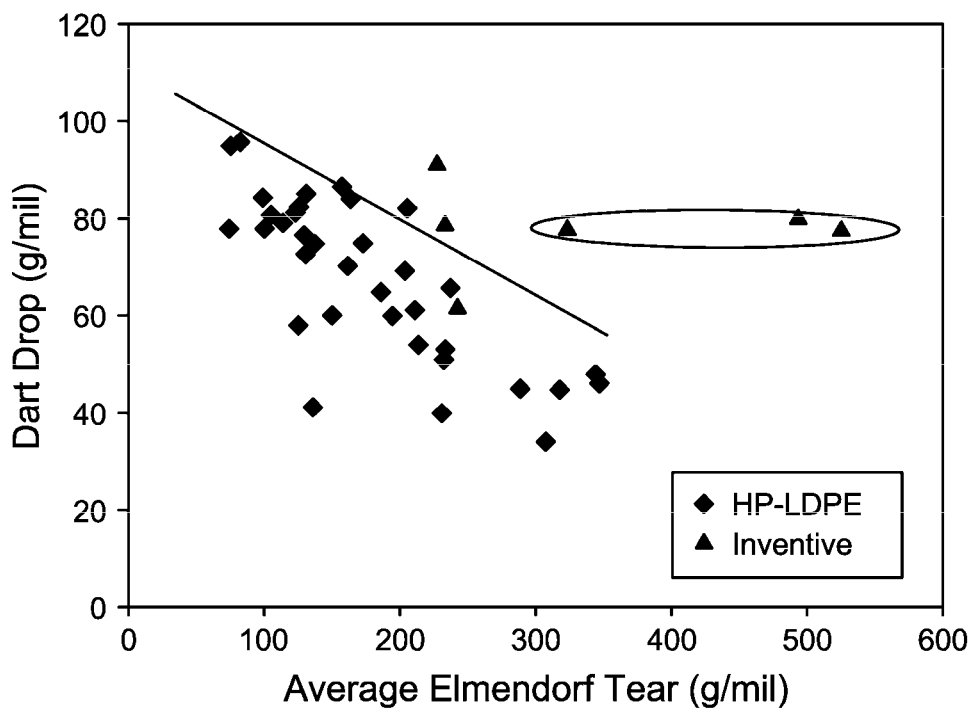
FIG. 14 shows a comparison Dart Drop of various LDPE resins and inventive resins as a function of Average Elmendorf Tear.

Inventive LCB m-LLDPE resins have superior toughness balance to HP-LDPE resins, which is demonstrated in FIG. 14. In FIG. 14, the circled data points correspond to LCB m-LLDPE resins: 1 g/10 min, 0.925 g/cm$^3$; and 0.4 g/10 min, 0.943 g/cm$^3$. The limit of the impact-tear resistance of the HP-LDPE resins is expressed by the relationship: Dart Drop (g/mil)=−8.09*[Average Elmendorf Tear (g/mil)]+853.81.

Figure 15:
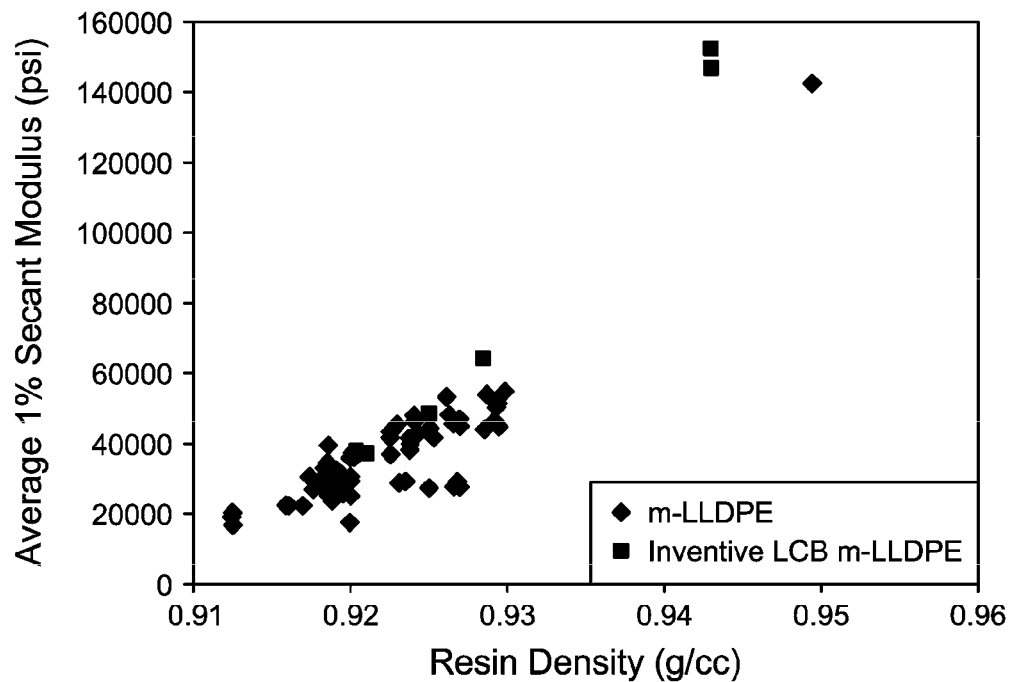
FIG. 15 shows a comparison of Average 1% Secant Modulus (psi) for various polyethylene resins and inventive resins as a function of resin Density.

Also, LCB m-LLDPE resins have superior film stiffness to m-LLDPE resins as shown by the data in FIG. 15. The 0.924-0.943 g/cm$^3$ LCB m-LLDPE resin converted into 0.75 mil film using 60 mil die gap. The 0.912-0.950 g/cm$^3$ m-LLDPE resins converted into 0.75-1 mil film using a 45-110 mil die gap as described above.

Figure 16A:
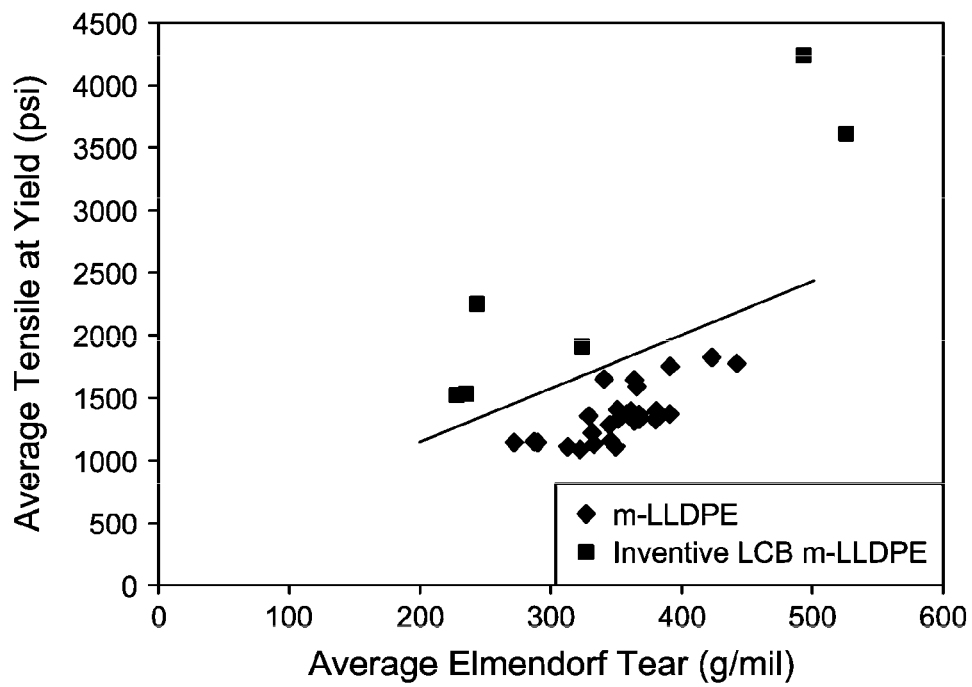
FIG. 16A and FIG. 16B shows a comparison of Average Tensile at Yield for various polyethylenes and inventive resins ("LCB m-LLDPE") as a function of Average Elmendorf Tear.
Figure 16B:
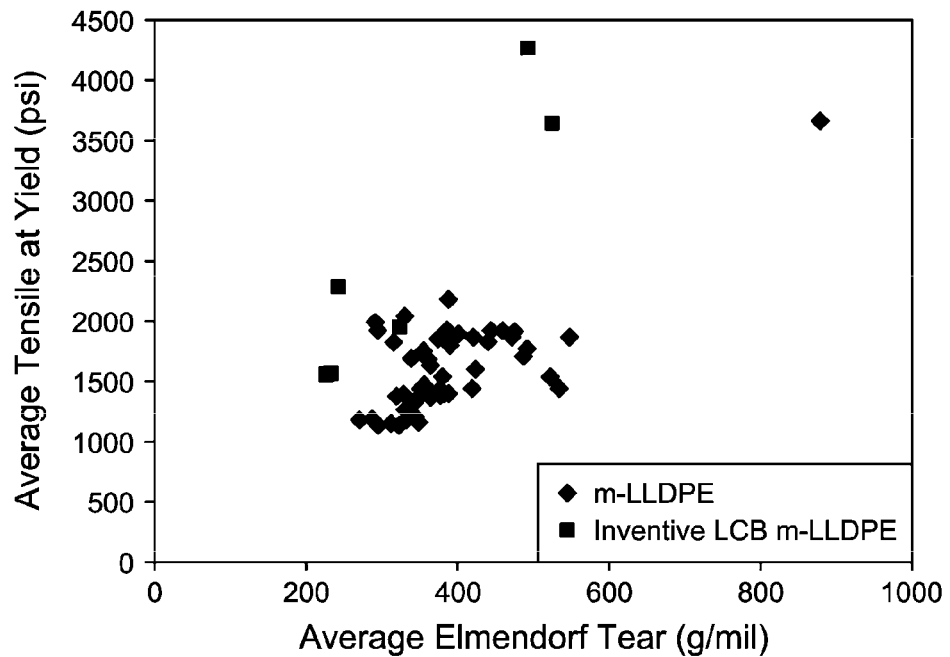

Finally, the inventive LCB m-LLDPE film have superior "lifting" ability (Tensile at Yield) to m-LLDPE film at any tear resistance, as shown by the data in FIGS. 16A and 16B. 0.915-0.923 g/cc m-LLDPE resins converted into 0.75-1 mil film using a 60 mil die gap. The regression line in FIG. 16A has the meaning: Line has the following definition: Tensile at Yield=4.274 (Elmendorf Tear)+300. The 0.912-0.950 g/cm$^3$ m-LLDPE resins were converted into 0.75-1 mil film using a 45-110 mil die gap as described above.

Figure 17:
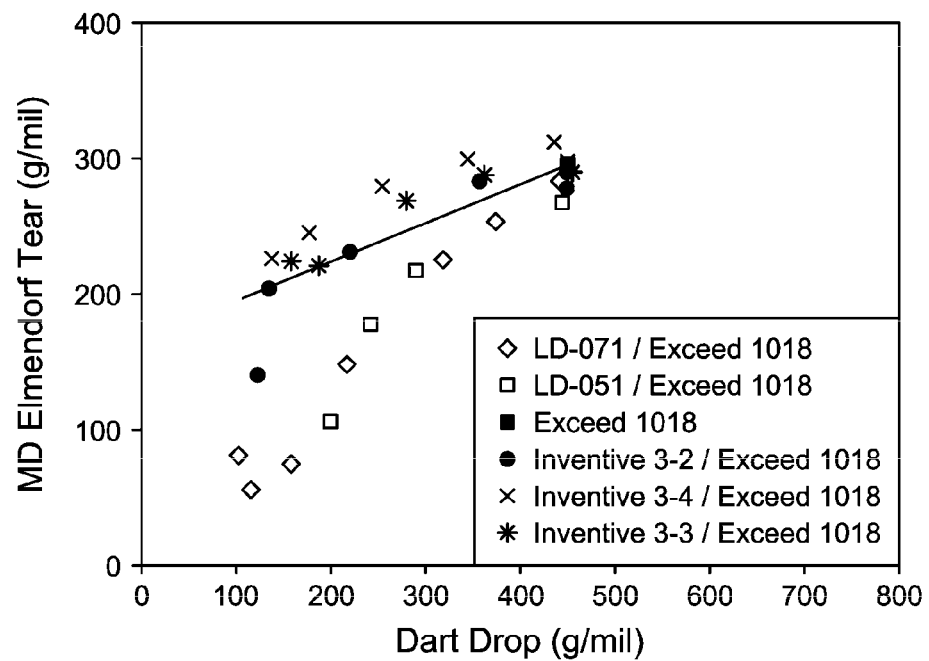
FIG. 17 shows a comparison of Dart Drop of various polyethylene resins and inventive resins as a function of MD Elmendorf Tear.

The inventive LCB m-LLDPE resins improve MD tear resistance at any impact resistance of films made from blends with m-LLDPE resins compared to that of films made from HP-LDPE/m-LLDPE blends. The data in FIG. 17 demonstrate this, For blends containing a 25%-60% of an ethylene-based copolymer resin, the regression line is MD Tear=0.3622 (Dart Drop)+164.44; and for blends containing a 15%-60% of an inventive ethylene-based copolymer resin, the regression line is MD Tear=0.2199 (Dart Drop)+196.59. Thus, the inventive films comprising blends of the ethylene-based copolymer (LCB m-LLDPE) and LLDPE fall above the lines.

For all jurisdictions in which the doctrine of "incorporation by reference" applies, all of the test methods, patent publications, patents and reference articles are hereby incorporated by reference either in their entirety or for the relevant portion for which they are referenced.

The invention claimed is:

1. An ethylene-based copolymer comprising 75.0 wt % to 99.5 wt % of ethylene-derived units and 0.5 wt % to 25.0 wt % of $C_3$ to $C_{20}$ olefin derived units; the ethylene-based copolymer having:
   a) a density in the range of from 0.900 to less than 0.950 g/cm$^3$;
   b) a g'(vis) of less than 0.80;
   c) a melt index, $I_2$, of from 0.25 to 1.5 g/10 min.;
   d) a Mw/Mn within a range from 3.0 to 6.0;
   e) a Mz/Mn of greater than 8.0; and
   f) an absence of a local minimum loss angle at a complex modulus, G*, of $1.00 \times 10^4$ to $3.00 \times 10^4$ Pa.

2. The ethylene-based copolymer of claim 1, wherein the ethylene-based copolymer has a complex modulus, $G^*_{50}$ of greater than $50.00 \times 10^3$ Pa.

3. The ethylene-based copolymer of claim 1, wherein the ethylene-based copolymer displays a multimodality in dissolution temperatures in a TREF analysis.

4. The ethylene-based copolymer of claim 3, wherein the ethylene-based copolymer has a $T_{90}$ to $T_{10}$ value of 5° C. or greater, wherein $T_{10}$ is the temperature at which 10 wt % of the eluted polymer is obtained, and $T_{90}$ is the temperature at which 90 wt % of the eluted polymer is obtained in a TREF analysis.

5. The ethylene-based copolymer of claim 4, wherein at least one of $T_{10}$ or $T_{90}$ is in the range of from 45° C. to 85° C.

6. The ethylene-based copolymer of claim 4, wherein $T_{90}$ is greater than 90° C.

7. The ethylene-based copolymer of claim 1, wherein if the ethylene-based copolymer comprises $C_x$ monomer derived units, wherein x represents the number of carbons in the $C_x$ monomer and is an integer in the range of from 3 to 20, then only short chain branches of the $C_{x-2}$ type are observed in the polymer.

8. The ethylene-based copolymer of claim 1, wherein the ethylene-based copolymer has a melt index ratio ($I_{21}/I_2$) within the range from 10.0 to 100.0.

9. The ethylene-based copolymer of claim 1, wherein the ethylene-based copolymer has a complex viscosity ratio of 50 or more.

10. The ethylene-based copolymer of claim 1, wherein the ethylene-based copolymer has within the range from 0.10 or 0.15 to 0.40 or 0.50 terminal vinyl groups per 1000 carbons.

11. The ethylene-based copolymer of claim 1, wherein the ethylene-based copolymers have an Mz value of greater than 250,000 g/mole or 300,000 g/mole or 350,000 g/mole, or 400.000 g/mole, or 450,000 g/mole.

12. The ethylene-based copolymer of claim 1, wherein the ethylene-based copolymer has an Mw of greater than 75,000 g/mol.

13. The ethylene-based copolymer of claim 1, wherein the ethylene-based copolymer has a g'(vis) of less than 0.65.

14. The ethylene-based copolymer of claim 1, wherein the ethylene-based copolymer has a g'(z avg) of less than 0.75.

15. The ethylene-based copolymer of claim 1, wherein the ethylene-based copolymer has a zero shear viscosity of 80,000 Pa·s or less, as determined by small angle oscillatory shear analysis.

16. The ethylene-based copolymer of claim 1, wherein when extruded through a blown film line the ethylene-based copolymer has an extruder motor load of less than 70 or 60 or 50% of the value when extruding commercial LLDPE having an $I_2$ of 1.0 g/10 min and density of 0.918 g/cm$^3$.

17. A film comprising at least 5 wt % of an ethylene-based copolymer comprising 75.0 wt % to 99.5 wt % of ethylene-derived units and 0.5 wt % to 25.0 wt % of $C_3$ to $C_{20}$ olefin derived units; the ethylene-based copolymer having:
   a) a density in the range of from 0.900 to less than 0.950 g/cm$^3$;
   b) a g'(vis) of less than 0.80;
   c) a melt index, $I_2$ of from 0.25 to 1.5 g/10 min.;
   d) a Mw/Mn within a range from 3.0 to 6.0;
   e) a Mz/Mn of greater than 8.0; and
   f) an absence of a local minimum loss angle at a complex modulus, G*, of $1.00 \times 10^4$ to $3.00 \times 10^4$ Pa;
   wherein the film has:
      (i) a 1% Secant Modulus MD of 30,000 psi or greater:
      (ii) an Elmendorf Tear MD value of 100 g/mil or greater, and
      (iii) a Dart Impact of 225 g/mil or greater.

* * * * *